United States Patent
Hunneche et al.

(10) Patent No.: US 11,219,690 B2
(45) Date of Patent: Jan. 11, 2022

(54) METHOD FOR THIOETHER CONJUGATION OF PROTEINS

(71) Applicant: Novo Nordisk Health Care AG, Zurich (CH)

(72) Inventors: Charlotte Schou Hunneche, Bagsvaerd (DK); Thomas Budde Hansen, Copenhagen N (DK); Ernst Broberg Hansen, Bagsvaerd (DK)

(73) Assignee: Novo Nordisk Healthcare AG, Zurich (CH)

( * ) Notice: Subject to any disclaimer, the term of this patent is extended or adjusted under 35 U.S.C. 154(b) by 0 days.

(21) Appl. No.: 15/103,482

(22) PCT Filed: Dec. 15, 2014

(86) PCT No.: PCT/EP2014/077777
§ 371 (c)(1),
(2) Date: Jun. 10, 2016

(87) PCT Pub. No.: WO2015/086853
PCT Pub. Date: Jun. 18, 2015

(65) Prior Publication Data
US 2016/0303248 A1    Oct. 20, 2016

(30) Foreign Application Priority Data

Dec. 13, 2013  (EP) ...................... 13197150

(51) Int. Cl.
*A61K 47/54* (2017.01)
*C07K 1/107* (2006.01)
*A61K 47/00* (2006.01)

(52) U.S. Cl.
CPC .......... *A61K 47/542* (2017.08); *A61K 47/545* (2017.08); *A61K 47/557* (2017.08); *C07K 1/1077* (2013.01)

(58) Field of Classification Search
None
See application file for complete search history.

(56) References Cited

U.S. PATENT DOCUMENTS

| 7,629,314 | B2 | 12/2009 | Cox, III |
| 2008/0200651 | A1 | 8/2008 | Ostergaard et al. |
| 2012/0178906 | A1* | 7/2012 | Cagnolini ............ A61K 51/088 530/345 |

FOREIGN PATENT DOCUMENTS

| CN | 103087183 A | 5/2013 |
| JP | 2004/508014 A | 3/2004 |
| JP | 2008546670 A | 12/2008 |
| WO | 99/03887 | 1/1999 |
| WO | 0042175 A1 | 7/2000 |
| WO | 2004/101597 A2 | 11/2004 |
| WO | 2005/070468 A2 | 8/2005 |
| WO | 2006/134173 A2 | 12/2006 |
| WO | 2007/003898 A1 | 1/2007 |
| WO | 2009/027369 A1 | 3/2009 |
| WO | 2011089250 A2 | 7/2011 |
| WO | 2011089255 A1 | 7/2011 |
| WO | WO 2011/089255 * | 7/2011 |
| WO | 2011101261 A2 | 8/2011 |
| WO | 2012010516 A1 | 1/2012 |
| WO | 2012/166622 A1 | 12/2012 |
| WO | WO 2013/067301 * | 5/2013 |

OTHER PUBLICATIONS

Sartorius Stedim Biotech Application Note (downloaded on Apr. 28, 2017 from http://microsite.sartorius.com/fileadmin/sartorius_pdf/alle/biotech/Appl_Crossflow_13_Recombinant_Protein_Concentration_SL-1048-e.pdf).*
Gagnon P, "Technology trends in antibody purification" Journal of Chromatography A,Year 2012,vol. 1221, pp. 57-70.
Sartorius Stedim Biotech. "Specifications Materials of construction,Hydrosart Ultrafiltration Cassettes"; Year 2011 Retrieved from the Internet on Mar. 28, 2014:; URL:http ://www.sartorius.com/fileadmin/fm-dam/sartorius_media/Bioprocess-Solutions/Purification_Technologies/Crossflow_Consumables/Standard_Cassettes/Data_Sheets/Data_Hydrosart_Ultrafilt_SPC2027-e.
Gilbert "Thiol/Disulfide Exchange Equilibria and Disulfide Bond Stability." Methods of Enzymology 1995 vol. 251 pp. 8-28.
Hu et al., "Influence of the Chemistry of Conjugation of Poly(ethylene glycol) to Hb on the Oxygen-Binding and Solution Properties of the PEG-Hb Conjugate," Biochemical Journal, 2005, vol. 392, No. 3, pp. 555-564.

* cited by examiner

*Primary Examiner* — Sergio Coffa
(74) *Attorney, Agent, or Firm* — Jianjie Hu

(57) ABSTRACT

The invention relates to methods for obtaining a protein conjugate wherein a cysteine residue of the protein serves as attachment point for the chemical moiety conjugated to the protein.

20 Claims, 8 Drawing Sheets
Specification includes a Sequence Listing.

A

B

A

B

A

B

A

B

SEQUENCE LISTING

```
<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125
```

```
Glu Asp Gly Ser Pro Arg Thr Gly Gln Ile Phe Lys Gln Thr Tyr Ser
            130             135             140

Lys Phe Asp Thr Asn Ser His Asn Asp Asp Ala Leu Leu Lys Asn Tyr
145             150             155                         160

Gly Leu Leu Tyr Cys Phe Arg Lys Asp Met Asp Lys Val Glu Thr Phe
                165             170                     175

Leu Arg Ile Val Gln Cys Arg Ser Val Glu Gly Ser Cys Gly Phe
            180             185                 190
```

METHOD FOR THIOETHER CONJUGATION OF PROTEINS

CROSS-REFERENCE TO RELATED APPLICATIONS

This application is a 35 U.S.C. § 371 National Stage application of International Application PCT/EP2014/077777 (WO 2015/086853), filed Dec. 15, 2014, which claims priority to European Patent Application 13197150.9, filed Dec. 13, 2013, the contents of which are incorporated herein by reference.

The instant application contains a Sequence Listing which has been submitted in ASCII format via EFS-Web and is hereby incorporated by reference in its entirety. Said ASCII copy, created on Jun. 9, 2016, is named 8695US01_SeqList.txt and is 3 kilobytes in size.

TECHNICAL FIELD

The present invention relates to improved methods for preparing protein conjugates with a thioether using a free cysteine of the protein as attachment point for a moiety of interest.

BACKGROUND

Protein conjugates have multiple functionalities in particularly in the pharmaceutical industry where the ability to covalently link various moieties to a therapeutic protein of interest and thereby improve the properties of the molecule of particular interests.

Conjugation of peptides is usually obtained by solid state synthesis while this approach is less attractive for larger proteins. When conjugation of larger polypeptides/protein is desired the process is complicated by the need of obtaining site specific conjugation in order to obtain a homogeneous product. Various technics have been developed providing means for conjugating to N- and C-terminal residues as well as internal amino acid residues.

For growth hormone proteins Gln and Lys residues have been successfully targeted as described in such as WO2005/070468 and WO2009/027369 wherein enzyme specificity to particular internal amino acid residues ensured site specific conjugation.

Site specific conjugation of proteins, including growth hormone, has previously been described in for example WO 99/03887 where site directed conjugation is obtained via an added cysteine residue by reacting the protein with a cysteine-reactive polymer or moiety. Prior to this, the protein is partly reduced with dithiothreitol (DTT) to improve PEGylation with the PEG-maleimide (or PEG-vinylsulfone), taking care not to reduce also the disulfide bonds of the protein. The publication further describes the difficulties in obtaining a high proportion of mono-PEGylated protein in the final product composition.

Different means to obtain selective reduction of an added cysteine is described also in WO 2006/134173 dealing primarily with factor VIIa, which also includes internal disulfide bonds. WO2010/089255 and WO2012/010516 disclose the use of an additional cysteine residue for conjugation of albumin binders and cholic acid residues, respectively.

Furthermore, cys conjugation may also be applied to proteins, antibodies or fragments hereof such as described in WO 2007/03898 and WO2012166622.

The reduction and conjugation steps are in themselves known chemical processes but the processes require a lot of handling rendering the processes time consuming and inefficient.

Therefore, in order to advance from research to development with cys conjugated compounds, there is an unmet need for providing methods that are efficient, economic and applicable in industry scale.

SUMMARY

The present application in an aspect relates to a method for preparing a protein conjugate wherein the protein (P) is covalently bound to a chemical moiety (Z) via a thioether, comprising the steps of;
a) obtaining a composition of a mixed di-sulfide comprising the protein,
b) adding a reducing agent to said protein composition,
c) allowing reduction to occur,
d) obtaining a solution comprising a reduced protein (P-SH),
e) removing molecules of the solution with a molecular weight below 10 kDa,
f) adding an activated chemical moiety (Z*) to the solution comprising the reduced protein
g) allowing a conjugation reaction to occur and
h) obtaining a preparation of said conjugated protein (P-S-Z).

The method may in certain embodiments involve the use of a cross flow filtration/tangential flow filtration system. In particular the reduction and conjugation reaction may according to the invention be performed in the retentate tank of a filtration system and when considered favourable the filtration system may be used throughout the process.

The method may further include steps of ultrafiltration and/or diafiltration. In situations where a specified concentration of one or more reactants are desired an ultrafiltration step can be applied. As an example the concentration of the mixed disulfide can be adjusted by a step of ultrafiltration to reach at least 100 µM, such as 150 µM, 250 µM, 350 µM or even such as above 400 µM, independently of the concentration of the mixed disulfide in the starting preparation. For a growth hormone the concentration may be at least 2 g/L, such as 5 g/L or such as 10 g/L independently of the concentration of the growth hormone in the starting preparation.

Diafiltrations may be used to remove small molecules from the filtration system and a relevant threshold, such as 10 kDa may be used but of course depending on the protein and reactants used.

The method applies a mixed di-sulfide as starting point, as this has been found to be reliable source of protein with a free cysteine, usually presented as a capped free cysteine wherein the Cap is derived from cysteine, cysteamine or glutathione.

The reducing agent and condition for reductions are to be favourable for the selective reduction of the mixed di-sulfide and phosphines, such as an triarylphosphine, and in particular disodium triphenylphosphine-3,3'-disulfonate (TPPDS) has been identified as an useful reducing agent. The inventors have found that the method of the present invention abolish the need for a high concentration of the reducing agent, although a more efficient process is obtained when the concentration of the reducing agent is at least equal to the concentration the protein (P-S-S-Cap).

As activated chemical moiety (Z*) a halogenated moiety may be used. When the activated chemical moiety is added to the reduced protein (step f) at least one (1) equivalent of the activated chemical moiety (Z*), relative to the amount of mixed disulfide is found to be more favourable.

As described herein the method may be applied for conjugation of a wide range of proteins and chemical moieties and provides an efficient and convenient method for obtaining such protein conjugates.

The invention may also solve further problems that will be apparent from the disclosure of the exemplary embodiments.

BRIEF DESCRIPTION OF DRAWINGS

FIG. 8A shows the relative content of reduced protein during conjugation under the conditions of experiments 5, 6 and 11 from table 2. FIG. 8B shows the relative content of reduced protein during the conjugation reaction of experiments 14, 15, 18 and 19 from table 2. The figures show the conversion of reduced GH-L101C-SH (after diafiltration) and addition of side chain. The reaction was monitored by AIE-HPLC, and the relative area % of the starting material is plotted versus reaction time.

Figure 1:
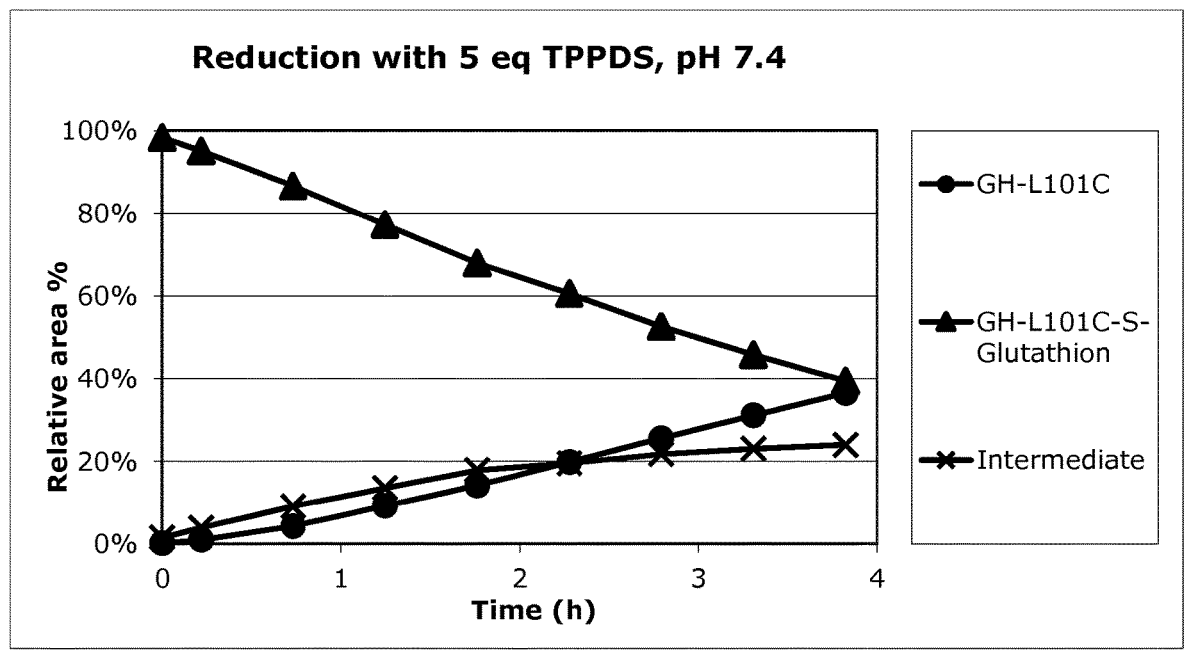
FIG. 1A shows the reduction of GH-L101C-S-Glutathion at a concentration of 2.4 g/L with 5 equivalents of TPPDS at pH 7.4. The reaction was followed by AIE-HPLC, and the relative area % of the starting material, reaction intermediate and product is plotted versus reaction time. ▲: GH-L101C-S-Glutathion, X: reaction intermediate, ●: GH-L101C-SH.
FIG. 1B shows the conjugation of side chain with the reduced GH-L101C-SH after reduction for 4 hours as shown in FIG. 1A. 2.2 equivalents of side chain are added directly to the reduction mix without any diafiltration. The relative area % of the starting materials and product is plotted versus reaction time. Area % of side chain is set to 100% at beginning of conjugation reaction. X: Side chain, ●: GH-L101C-SH, ▲: GH-L101C-S-Side chain, ○: GH-L101C-S-Glutathion, ▲: reaction intermediate.
Figure 1:
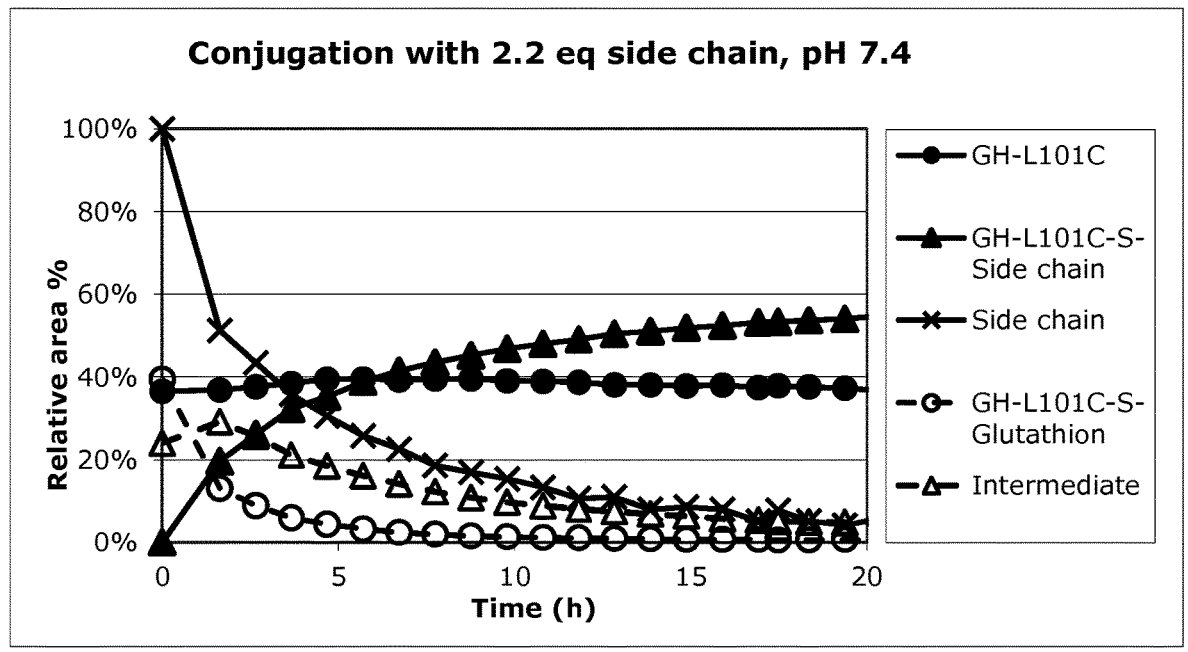

SEQ ID NO: 1-human growth hormone AA 1-181 FPTIPLSRLF DNAMLRAHRL HQLAFDTYQE FEEAYIPKEQ KYSFLQNPQT SLCFSESIPT PSNREETQQK SNLELLRISL LLIQSWLEPV QFLRSVFANS LVYGASDSNV YDLLKDLEEG IQTLMGRLED GSPRTGQIFK QTYSKFDTNS HNDDALLKNY GLLYCFRKDM DKVETFLRIV QCRSVEGSCG F Definitions The term "polypeptide" and "peptide" as used herein means a compound composed of at least two amino acids connected by amide (or peptide) bonds.

The term "amino acid" includes the group of the amino acids encoded by the genetic code which are herein referred to as standard amino acid. Further included are natural amino acids which are not encoded by the genetic code, as well as synthetic amino acids.

Commonly known natural amino acids include γ-carboxyglutamate, hydroxyproline, ornithine, sarcosine and phosphoserine. Commonly known synthetic amino acids comprise amino acids manufactured by chemical synthesis, such as Aib (alpha-aminoisobutyric acid), Abu (alpha-aminobutyric acid), Tle (tert-butylglycine), β-alanine, 3-aminomethyl benzoic acid, anthranilic acid.

The term "protein" as used herein means a biochemical compound consisting of one or more polypeptides.

The term "growth hormone" is used to describe wild type growth hormones such as human growth hormone identified by SEQ ID NO 1.

The term "growth hormone variant" as used herein means a growth hormone protein which has an amino acid sequence which is derived from the structure of a naturally occurring growth hormone, for example that of human growth hormone identified by SEQ ID NO 1, by deleting, adding and/or substituting at least one amino acid residue occurring in the natural human growth hormone and/or by adding at least one amino acid residue. The term is also used for a modified growth hormone protein wherein one or more amino acid residues of the growth hormone sequence has/ have been substituted by other amino acid residues and/or wherein one or more amino acid residues have been deleted from the growth hormone and/or wherein one or more amino acid residues have been added and/or inserted to the growth hormone.

With the term "growth hormone compound" as used herein, is meant a growth hormone molecule retaining at least some of the functionalities of human growth hormone identified by SEQ ID NO 1 and the overall structure hereof including the two intra-molecular disulfide bonds connecting C53 with C165 and C182 with C189 or corresponding amino acid residues in growth hormone variants. Such molecules may be growth hormone variants, growth hormone derivatives or growth hormone fusions and derivatives and fusions of growth hormone variants.

As used herein the term "growth hormone derivative" is thus a human growth hormone or a human growth hormone analogue/variant which comprises at least one covalent modification attached to one or more amino acids, such as to one or more amino acid side chains of the growth hormone or growth hormone variant or analogue wherein the modification(s) are in the form of attachment of amides, carbohydrates, alkyl groups, esters, PEGylations and the like.

Such growth hormone derivatives may be term "alkylated growth hormone" covering modification of growth hormone by attachment of one or more chemical moieties, optionally via a linker to the growth hormone protein.

The chemical moiety may be described as a property modifying entity. The chemical moiety may be lipophilic by, including a fatty acid, and attached to the growth hormone protein or analogue, optionally via a linker. The chemical moiety, including any optionally linker may be described as the "side chain". In the present application, linking the chemical moiety to the free cysteine, the "side chain" will be attached as extension of the cysteine amino acid residue.

The term "growth hormone fusions" as used herein refers to a protein molecule where a growth hormone compound (wild type or variant) is expressed as fusion protein with an polypeptide of interested and thus linked by a traditional peptide bond.

The term "drug", "therapeutic", "medicament" or "medicine" when used herein refer to an active ingredient used in a pharmaceutical composition, which may be used in therapy.

The term "ultrafiltration" is used to describe the process of filtering a solution using an appropriate membrane or filter, where the process usually due to a pressure difference results in a reduced volume of the solution with the result that the molecule of interest in the solution is up-concentrated.

The term "diafiltration" is used to describe the process of filtering a solution using an appropriate membrane or filter, where the process involves a change in excipients of the solution as the starting solution is exchanged with a new solution as solution drained from the system is substituted with the new solution. In most systems the solution is considered exchanged when the 5× the volume of the starting solution has been drained from the system and the system filled with equal amount of the new solution. By this process the molecule of interest is transferred from one solution to a new solution.

DESCRIPTION

The present invention in an aspect relates to a method for preparing a protein conjugate wherein the protein (P) is covalently bound to a chemical moiety (Z) via a thioether. The method may start from a composition of a mixed di-sulfide comprising the protein subject to conjugation. This disulfide is reduced to obtain a protein with a free cysteine (P-SH) suited for conjugation. The conjugation reaction is subsequently performed by adding an activated chemical moiety (Z*) to the reduced protein leading to the formation of the conjugated protein (P-S-Z). As described herein the individual steps have been optimized to obtain an efficient process for preparation of protein conjugates.

The present application relates to a method for preparation of a protein conjugate where the protein (P) is linked to a chemical moiety (Z) via a sulfur atom forming a thiol ether.

As described herein below the protein may be any protein of interest and includes in particular therapeutic proteins such as growth hormone and growth hormone variants.

In one embodiment the invention relates to a method of preparing a protein conjugate where the chemical moiety is linked to the protein via a cysteine residue of the protein. The sulfur atom thus provides the attachment point for the chemical moiety to be attached to the protein, whereby the protein and the chemical moiety are covalently linked via a thioether.

"Free cysteines" have been found to be suitable attachment points for conjugations of various property modifying groups. A free cysteine herein refers to a cysteine residue that is not engaged in an ordinary di-sulfide bond between two cysteine's of one or two polypeptides. Usually a free cysteine will be a cysteine that has been introduced in a polypeptide sequence of interest by site-selective mutagenesis, but some proteins may alternatively include a cysteine in a suitable position. As described in the background, an added cysteine may be a suitable attachment point for a property modifying group to a protein. By introducing a cysteine residue a free cysteine is usually obtained as no partner for forming a di-sulfide bond is present in the protein.

In one embodiment the invention relates to a method for preparing a protein conjugate, wherein the protein (P) is covalently bound to a chemical moiety (Z) via a thioether, comprising the steps of;
a) obtaining a composition of a mixed di-sulfide comprising the protein,
b) adding a reducing agent to said composition obtaining a reduction mix,
c) allowing reduction to occur,
d) obtaining a solution comprising a reduced protein (P-SH),
e) optionally removing molecules of the solution with a molecular weight below 10 kDa,
f) adding an activated chemical moiety (Z*) to the solution comprising the reduced protein obtaining a conjugation mix,
g) allowing conjugation reaction to occur and
h) obtaining a preparation of said conjugated protein (P-S-Z).

The method allows for selective reduction of the free cysteine and thereby a selective chemical conjugation of the protein.

Mixed Disulfide

Disulfides (R1-S-S-R2) are covalent bindings of two sulfur atoms which may be present in different (or the same) molecules. In proteins, cysteine residues may be linked via a disulfide bond also called a cystine.

In order to be an effective target of a conjugation reaction the free cysteine must be in the reduced form. A protein with a free cysteine, may for the same reason, be difficult to produce, and is thus frequently obtained as a mixed disulfide including a small organic moiety. Mixed disulfides are molecules including a di-sulfide, similar to the di-sulfide bond between two cysteine amino acid residues, each included in a polypeptides sequence (which may be the same or not). The small organic moiety is herein referred to as a Cap and the mixed disulfide is thus a protein-S-S-Cap molecule. In the present application the term "mixed di-sulfides" is used for molecules which comprise a disulfide bond linking two different entities which are not both polypeptides, although the molecules may additionally include "ordinary" disulfides bonds in addition to the mixed disulfide.

In one embodiment the method of the invention includes a step of reduction of a protein-S-S-Cap molecule as the protein subject to conjugation is obtained in the form of a composition of protein-S-S-Cap molecule.

As described above, the Cap is usually derived from a small organic moiety, including at least one sulfur atom that is part of the disulfide bond of the mixed di-sulfide. Such organic moieties can exist as monomers in the reduced form or as dimers in the oxidised form. In the mixed disulfide, -S-Cap is thus the oxidised form of the monomer or half a dimer. In one embodiment the S-Cap is derived from cysteine/cystine, cysteamine/cystamine (which is a decarboxylated cystine) or glutathione (G-SH)/glutathione disulfide (GS-SG), and the mixed disulfide is thus in an embodiment selected from Protein-S-S-cys, Protein-S-S-cyst or Protein-S-S-G, where cys refers to half of a cystine, cyst refers to half of cystamine and G refers to half of glutathione disulfide. In other words, in one embodiment the Cap of protein-S-S-Cap is derived from cysteine, cysteamine or glutathione.

As described above the aim of the reduction is to obtain a molecule with a free reduced cysteine (—SH) that is reactive in a conjugation reaction.

In one embodiment the mixed disulfide is a protein-S-S-Cap molecule wherein the protein-S is derived from a protein comprising a free cysteine.

In one embodiment the invention relates to a method for preparing a protein conjugate wherein the protein (P) is covalently bound to a chemical moiety (Z) via a thioether, comprising the steps of;
a) obtaining a composition of a mixed di-sulfide comprising the protein,
b) adding a reducing agent to said protein composition,
c) allowing reduction to occur,
d) obtaining a solution comprising a reduced protein (P-SH),
e) optionally removing molecules of the solution with a molecular weight below 10 kDa,
f) adding an activated chemical moiety (Z*) to the solution comprising the reduced protein
g) allowing conjugation reaction to occur and
h) obtaining a preparation of said conjugated protein (P-S-Z).

Each step will be further explained here below and exemplified in the Examples.

Growth Hormone Proteins

As described above the aim of the reduction is to obtain a protein molecule with a free reduced cysteine (—SH) that is reactive in a conjugation reaction.

In one embodiment the mixed disulfide is a protein-S-S-Cap molecule wherein the protein-S is derived from a protein comprising a free cysteine. In a further embodiment the protein is a growth hormone.

The structure of growth hormone proteins is composed of four helixes (helix 1-4) connected by three loops (L1-3), and a C-terminal segment. In human growth hormone (SEQ ID NO 1) helix 1 is defined by AA residue 6-35, helix 2 is defined by AA residues 71-98, helix 3 is defined by AA residue 107-127 and helix for is defined as AA residues 155-184.

As wild type human growth hormone includes no free cysteines, the present invention mainly relates to growth hormone variants including an additional cysteine providing a free cysteine. The method may be applied in the process of preparing growth hormone conjugates or derivatives using such a free cysteine. Such derivatives may be obtained by alkylation of a free thiol group introduced via single amino acid substitutions in the growth hormone sequence.

The growth hormone may in an embodiment be a growth hormone fusion, e.g. a protein molecules that include a growth hormone sequence linked to a second protein sequence by means of a peptide bond. Fusions are usually obtained by expression of the fusion protein using a recombinant expression vector linking a DNA sequence encoding said growth hormone sequence with a DNA sequence encoding said second protein optionally including a linker sequence. Growth hormone fusions include, but are not limited to, fusions comprising an antibody Fc region or regions and/or an albumin protein.

The term "growth hormone compound" as used herein collectively refers to a growth hormone molecule retaining substantially the functional characteristics of mature human growth hormone identified by SEQ ID NO 1. The compound may thus be a growth hormone, a growth hormone fusion protein, a growth hormone variant or analogue or a growth hormone derivative including also acylated or alkylated growth hormone.

In one embodiment a growth hormone analogue according to the invention comprises less than 8 modifications (substitutions, deletions, additions) relative to human growth hormone.

In one embodiment a growth hormone analogue comprises less than 7 modifications (substitutions, deletions, additions) relative to human growth hormone. In one embodiment a growth hormone analogue comprises less than 6 modifications (substitutions, deletions, additions) relative to human growth hormone.

In one embodiment a growth hormone analogue comprises less than 5 modifications (substitutions, deletions, additions) relative to human growth hormone. In one embodiment a growth hormone analogue comprises less than 4 modifications (substitutions, deletions, additions) relative to human growth hormone. In one embodiment a growth hormone analogue comprises less than 3 modifications (substitutions, deletions, additions) relative to human growth hormone. In one embodiment a growth hormone analogue comprises less than 2 modifications (substitutions, deletions, additions) relative to human growth hormone.

In a series of embodiment the growth hormone analogue of the growth hormone is at least 95, 96, 97, 98 or 99% identical to human growth hormone identified by SEQ ID NO: 1.

The growth hormone compound preferably has increased plasma half-life ($T_{1/2}$) compared to wild type human growth hormone. This may be achieved by various means known to the person skilled in the art, such as amino acid substitutions stabilizing the protein from degradation. Increased circulation time of a growth hormone compound may also be obtained by linkage covalently or non-covalently to serum proteins. Serum albumin may be used by direct conjugation (optionally including a linker) or by protein fusion with a growth hormone or variant thereof. Alternatively chemical linkage to albumin may also be considered as well as fusion or linkage with antibody Fc regions. Non-covalent attachment to albumin may be obtained through the use of albumin binders such as alkyl groups covalently bound to a growth hormone or variants thereof.

In one embodiment the growth hormone is a variant that is stabilized towards proteolytic degradation (by specific mutations), and such variants may be further be alkylated in one or more amino acids of the growth hormone protein.

Non-limiting examples of growth hormone proteins that are stabilized towards proteolytic degradation (by specific mutations) may be found in WO 2011/089250.

Protease-stabilized growth hormone protein variants include variants where an additional disulfide bridge is introduced. The additional disulfide bridge preferably connects L3 with helix 2. This may be obtained by introducing two extra cysteine amino acid residues, which in preferred embodiments are substituted for the wild type amino acid residue in positions corresponding to AA84 or AA85 in H2 and AA143 or AA144 in L3 of SEQ ID No. 1. The growth hormone variant may thus according to the invention preferably comprise a pair of mutations corresponding to L73C/S132C, L73C/F139C, R77C/I138C, R77C/F139C, L81C/Q141C, L81C/Y143C, Q84C/Y143C, Q84C/S144C, S85C/Y143C, S85C/S144C, P89C/F146C, F92C/F146C or F92C/T148C in SEQ ID No.1. In a further embodiment the growth hormone variant comprises a pair of mutations corresponding to L81C/Y143C, Q84C/Y143C, S85C/Y143C, S85C/S144C or F92C/T148C in SEQ ID No. 1.

In one embodiment the growth hormone is a growth hormone variant, suited for mono-substitution/site specific modification such as alkylation of one chemical moiety to a free cysteine introduced by mutation possibly in addition to any protease stabilizing mutations described above. A non-limiting list of growth hormone variants suitable for alkylation may be found in WO2011/089255.

In a further embodiment the protein is a growth hormone variant including a free cysteine. In a further embodiment the protein is a growth hormone variant including a free cysteine introduced in human growth hormone identified by SEQ ID NO.: 1. In a further embodiment the protein is a growth hormone variant including a cysteine mutation selected from the group of: T3C, P5C, S7C, D11C, H18C, Q29C, E30C, E33C, A34C, Y35C, K38C, E39C, Y42C, S43C, D47C, P48C, S55C, S57C, P59C, S62, E65C, Q69C, E88C, Q91C, S95C, A98C, N99C, S100C, L101C, V102C, Y103C, D107C, S108C, D112C, Q122C, G126C, E129C, D130C, G131C, P133C, T135C, G136C, T142C, D147C, N149C, D154C, A155C, L156C, R178C, E186C, G187C and G190C. In a further embodiment the protein is a growth hormone variant including a cysteine mutation selected from the group of: T3C, P5C, S7C, D11C, H18C, Q29C, E30C, E33C, A34C, Y35C, E88C, Q91C, S95C, A98C, N99C, S100C, L101C, V102C, Y103C, D107C, S108C, D112C, Q122C and G126C.

In further embodiments the free cys mutation is located within AA 93-106 in hGH or corresponding residues in hGH variants. In further specified embodiments the free cys mutation is located within L2, such as within AA 99-106 or AA 99-103 or corresponding residues.

In further embodiment the free cys mutation is selected from the group of: E30C, Y42C, S55C, S57C, S62C, Q69C, S95C, A98C, N99C, L101C, V102C and S108C.

In a further embodiment the single cys mutation is E30C. In further embodiment the single cys mutation is Y42C. In a further embodiment the single cys mutation is S55C. In a further embodiment the single cys mutation is S57C. In a further embodiment the single cys mutation is S62C. In a further embodiment the free cys mutation is Q69C. In further embodiment the free cys mutation is S95C. In a further embodiment the free cys mutation is A98C. In further embodiment the free cys mutation is N99C. In a further embodiment the free cys mutation is S100C. In a further embodiment the free cys mutation is L101C. In a further embodiment the free cys mutation is V102C. In a further embodiment the free cys mutation is S108C.

In a further embodiment the protein is a growth hormone variant including a cysteine mutation selected from Y42C and L101C.

Reducing Agent

In order to obtain a protein with a reactive sulfur atom a reducing agent is added to the mixed disulfide composition, and the mixture is incubated to allow the reduction to occur to obtain a protein with a reactive sulfur atom e.g. a reduced protein of the format: protein-S-H. The steps described are a) obtaining a composition of a mixed di-sulfide comprising the protein, b) adding a reducing agent to said protein composition, c) allowing reduction to occur and obtaining a solution comprising a reduced protein (P-SH).

The reducing agent may be chosen between a plurality of available reducing agents and only a few are mentioned herein, knowing that the person skilled in the art will be able to choose from a much larger repertoire of reducing agents.

In one embodiment the reducing agent is a redox buffer selected from the group of gluthathione, gama-glytamylcysteine, cysteinylglycin, cysteine, N-actylcystein, cysteamine and lipamide.

In one embodiment a thiol disulfide redox catalyst is included, such as an enzyme, such as a glutaredoxin.

In one embodiment the reducing agent is selected from a small molecule reducing agents such as DTT.

In one embodiment the reducing agent is a phosphine, such as an aromatic phosphine, such as a triarylphosphine, such as a substituted triarylphosphine, such as trisodium triphenylphosphine-3,3',3"-trisulfonate (TPPTS) or such as disodium triphenylphosphine-3,3'-disulfonate (TPPDS).

Once the mixed di-sulfide has been reduced a solution comprising a reduced protein (P-SH) has been obtained. Before the subsequent conjugation it may be beneficial to remove the reducing agent and/or the released Cap molecule. In one embodiment, an optional step of removing small molecules, such as molecules with a molecular weight below 10 kDa from the solution comprising the reduced protein (P-SH) may be included. In one embodiment molecules with a molecular weight below 10 kDa are removed from the solution comprising the reduced protein by diafiltration.

Chemical moiety (Z)

In a conjugation reaction a chemical moiety is covalently bonded to the sulfur atom of the free cysteine of the reduced protein (protein-SH).

The chemical moiety may be any moiety suitable for conjugation to a protein, such as a property modifying moiety. The property modifying moiety may be a chemical moiety capable of altering one of more features of the protein of interest. In one embodiment the chemical moiety is a property-modifying group, such as a chemical moiety capable of stabilizing the protein, increasing the circulatory half-life or increasing potency. In one embodiment the chemical moiety is a protracting agent. In one embodiment the chemical moiety (Z) is an albumin binder (AB). In order for the conjugation to occur effectively, the chemical moiety may be used in an activated form (Z*). In the method according to the invention as described herein above, an activated chemical moiety (Z*) is added to the solution comprising the reduced protein and the conjugation of the chemical moiety to the reduced protein results in preparation of a conjugated protein (P-S-Z). Thus the method according to the invention includes the further steps of: adding an activated chemical moiety (Z*) to the solution comprising the reduced protein, allowing conjugation reaction to occur and obtaining a preparation of said conjugated protein (P-S-Z).

In summary of the above description, the present invention relates to a method for preparing a protein conjugate wherein the protein (P) is covalently bound to a chemical moiety (Z) via a thioether, comprising the steps of;
a) obtaining a composition of a mixed di-sulfide comprising the protein,
b) adding a reducing agent to said protein composition,
c) allowing reduction to occur,
d) obtaining a solution comprising a reduced protein (P-SH),
e) optionally removing molecules of the solution with a molecular weight below 10 kDa,
f) adding an activated chemical moiety (Z*) to the solution comprising the reduced protein
g) allowing conjugation reaction to occur, such as a selective chemical conjugation, and
h) obtaining a preparation of said conjugated protein (P-S-Z).

The chemical moiety may be any moiety suitable for conjugation to a protein, such as a property modifying moiety. The property modifying moiety may be a chemical moiety capable of altering one of more features of the protein of interest. In one embodiment the chemical moiety is a property-modifying group, such as a chemical moiety capable of stabilizing the protein, increasing the circulatory half-life or increasing potency. In one embodiment the chemical moiety is an albumin binder. In order for the conjugation to occur effectively, the chemical moiety may be used in an activated form. In the method according to the invention as described herein above, an activated chemical moiety is combined with the reduced protein and the conjugation of the chemical moiety to the reduced protein results in preparation of a conjugated protein via a sulfur atom.

The chemical moiety is preferably an activated chemical moiety, which means a moiety which is capable of reacting with the protein-SH forming a protein-S-chemical moiety molecule. Such activated chemical moieties may include soft electrophilic alkylation reagents including a maleimide or haloacetyl groups, which are known in the art.

In one embodiment the activated chemical moiety (Z*) is a halogenated chemical moiety (Z-halo), such as a halogenated property-modifying group, such as a halogenated protracting agent. The halogenated chemical moiety (Z-halo) may include Br, I or Cl. If one is preferred a specific activation reaction may be performed prior to the conjugation and prior to adding the chemical moiety to the reduced protein.

In one embodiment the activated chemical moiety (Z*) is a halogenated albumin binder (AB-halo). In one embodiment the chemical moiety (Z*) is an albumin binder halogenated including Br, I or Cl, such as described in WO2010/089255. In one embodiment the activated chemical moiety is an iodoacetamide, such as an iodoacetamide of an albumin binder side chain.

In one embodiment the activated chemical moiety (Z*) is a maleimide substituted chemical moiety (Z-maleimide), such as a maleimide substituted property-modifying group, such as a maleimide substituted protracting agent. In one embodiment the activated chemical moiety (Z*) is maleimide substituted albumin binder, such as described in WO2010/089255).

The reduction and conjugation reactions described in Examples 2 and 3, include reaction of reduced Growth hormone L101C with a halogenated albumin binder side chain, wherein the halogen is Iodine.

In one embodiment the albumin binding side chain may be is selected from:

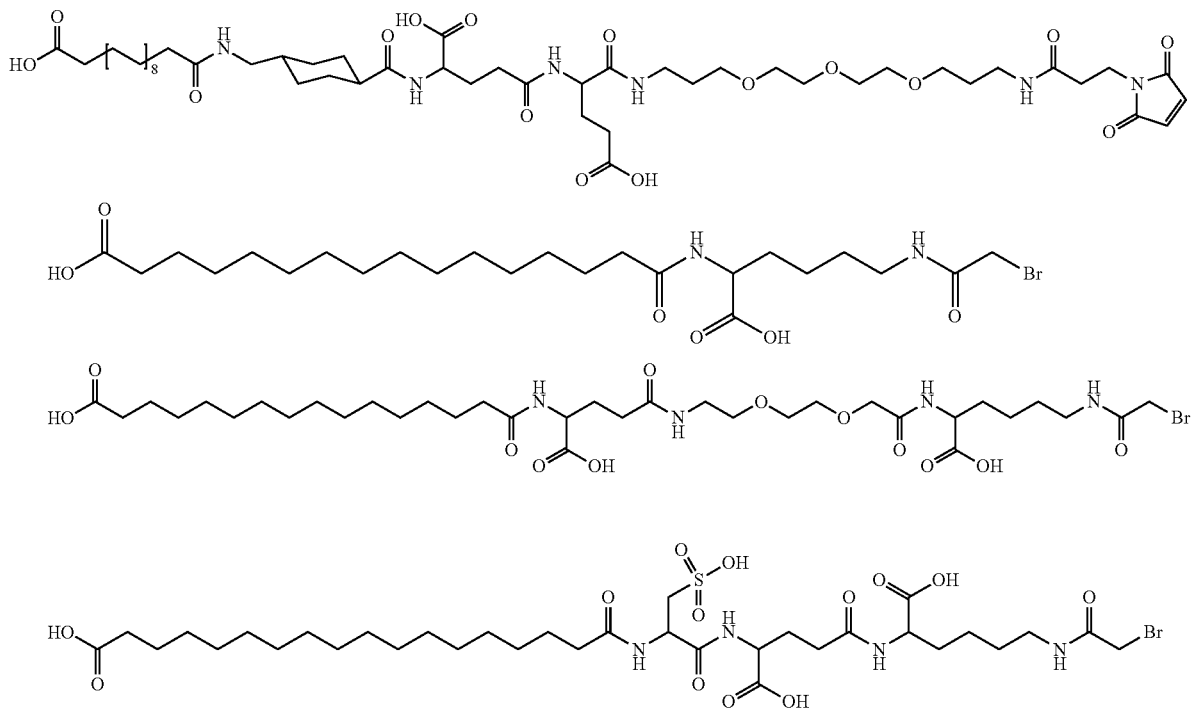

-continued

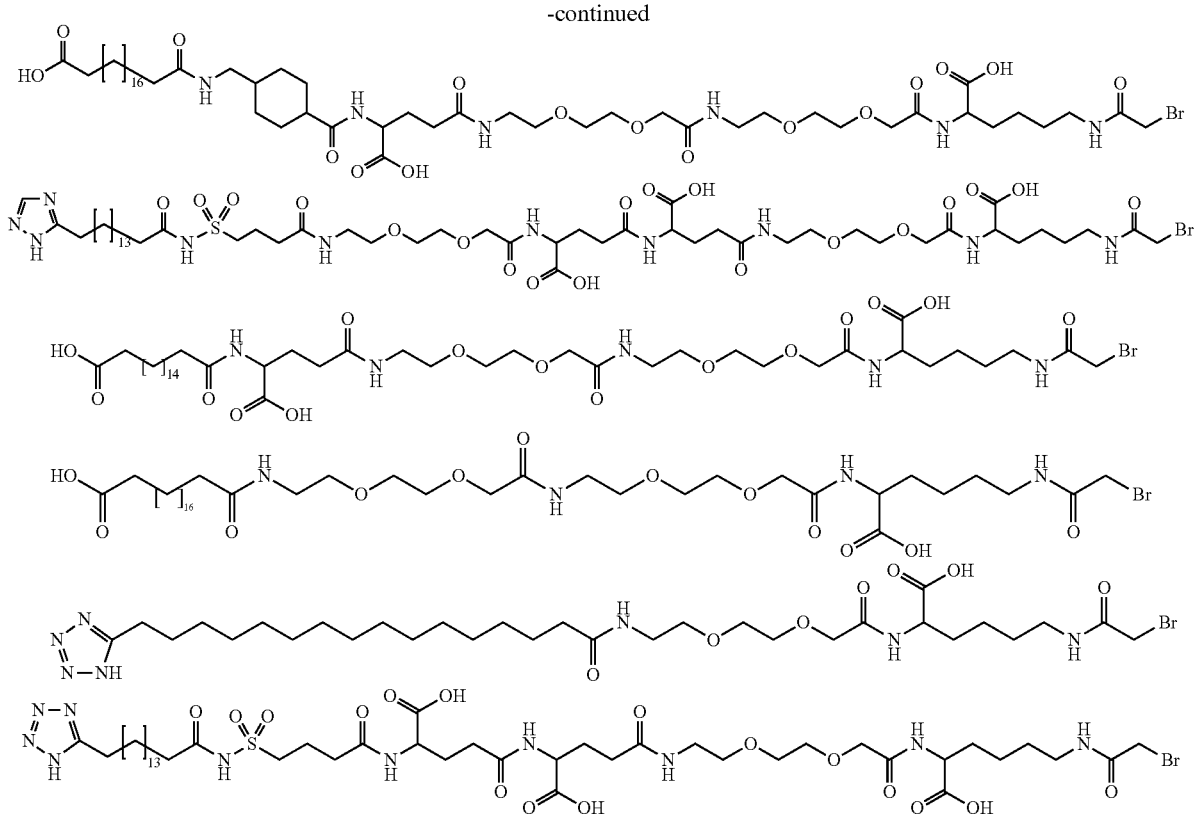

Further albumin binding side chains are described in WO2010/089255. In one embodiment the activated albumin side chain is an iodide version of the above. Such iodide moieties may be obtained by dissolving a halogenated (Br or Cl) chemical moiety in a KI (potassium iodide) solution providing an iodoacetamide.

Further examples of chemical moieties include PEG molecules, serum albumin, albumin binders, Fc, domains, the growth hormone binding protein, AA polymers (XTEN technology, Amunix, and PASylation®, XL-protein) and carbohydrate groups such as heparosan and hydroxyethyl-starch.

As described herein below the effectiveness of the conjugation step may depend on the ratio of reduced protein (P-SH) and activated chemical moiety (Z*).

Composition of the Mixed Di-Sulfide

The composition of the mixed di-sulfide comprising the protein to be conjugated at a free cysteine is preferably obtained as a purified composition comprising only minor amounts of other proteins or impurities and it is submitted that the skilled person will know of methods for producing and purifying proteins with a free cysteine as part of a mixed di-sulfide.

In one embodiment the mixed di-sulfide composition has a protein concentration of 5-4000 μM, 25-1000 μM, 50-850 μM, 100-600 μM, 250-600 μM or 250-500 μM. In further embodiments it is preferred that the concentration of the protein is above 100 μM, such as 150 μM, 250 μM, 350 μM or even such as above 400 μM.

In an embodiment where the mixed disulfide is a growth hormone or growth hormone variant the concentration is preferably 0.1-100 g/L, 0.5-25 g/L, 1-20 g/L, 2-15 g/L, 5-15 g/L or such as 5-12 g/L. In one embodiment the hGH composition has a concentration of at least 2.5 g/L, or such as at least 4.0 g/L, or such as at least 8.0 g/L or such as at least 10 g/L. It is also noted that the concentration can be adjusted by including an extra step whereby a preparation of the mixed di-sulfide is either diluted or up-concentrated to reach a preferred concentration of the protein. In one embodiment the method include a step of ultrafiltration of a mixed di-sulfide preparation producing the composition of the mixed disulfide composition.

In one embodiment the mixed di-sulfide composition has a pH which is suited for reduction of the protein and/or subsequently for the reduced protein to be conjugated, such as a pH of 4-10, such as 5-9 or 6-8. In a further embodiment the pH may be 7.0-8.0, or 7.2-7.8 or 7.3-7.6 such as around 7.4-7.5.

In one embodiment the mixed di-sulfide composition has a conductivity of around 5-50 mS/cm at 22° C., or such as 5-25 mS/cm at 22° C. or conductivity around 10 mS/cm at 22° C.

In one embodiment the mixed di-sulfide composition comprises a buffer.

In one embodiment the mixed di-sulfide composition comprises a buffer selected from the group consisting of: BES, HEPES, MES, Phosphate, Citrate, Bis-Tris and triethanolamine.

In one embodiment the mixed di-sulfide composition comprises 5-50 mmol/kg triethanolamine, such as 10-25 mmol/kg triethanolamine or such as around 20 mmol/kg triethanolamine.

In one embodiment the mixed di-sulfide composition comprises a salt.

In one embodiment the mixed di-sulfide composition comprises a salt selected from the group consisting of: Sodium, Ammonium, Guanidinium, and Potassium salts.

In one embodiment the mixed di-sulfide composition comprises a salt selected from the group consisting of: Sulfate, Acetate, and Halogenide salts.

In one embodiment the mixed di-sulfide composition comprises a salt selected from the group consisting of: Sodium Sulfate, Sodium Acetate, Ammonium Acetate, Guanidinium Hydrochloride, KI, and NaCl.

In one embodiment the mixed di-sulfide composition comprises NaCl.

In one embodiment the mixed di-sulfide composition comprises 25-500 mmol/kg NaCl, such as 50-250 mmol/kg, such as 75-100 mmol/kg NaCl or such as around 80 mmol/kg NaCl.

Method Steps

In the above general description the components used in the method are described with some variability. Additional points of variability with-in the scope of the invention is the duration of the process step, the use of different concentrations of each component and the excipients of the solutions the components are provided in and the excipients of the solutions that each method step is performed in.

Although the skilled person will know that further variation may be possible the following description further describes embodiments that the inventors have found particularly favourable. Details for illustrating the processes can be found in the examples.

Adding the Reducing Agent

In order to have an effective reduction of the mixed di-sulfide an excess of the reducing agent in molar concentrations is usually applied. By addition of the reducing agent to the composition of the mixed disulfide a reduction mix is obtained. The amount of reducing agent may be expressed in equivalents of the amount of the mixed di-sulfide (or P-S-S-Cap), such that in the case where the amount of reducing agent is 1 equivalent of the amount of the mixed di-sulfide, the molar concentrations of the mixed di-sulfide and the reducing agent in the mixture are equal.

In one embodiment the amount of the reducing agent added in step b) is at least 2 equivalents of the amount of the mixed di-sulfide (or P-S-S-Cap), such as 3-20 equivalents, such as 4-15 equivalents or such as 5-10 equivalents. In one embodiment 2-12 equivalents of reducing agent is added. In one embodiment 2-10 equivalents of reducing agent is added.

In one embodiment 3-7 or 4-6 equivalents of reducing agent is added.

As the reducing agent may be a costly resource it is advantageous to reduce the amount required, which as described herein is possible if the process steps are optimized. An effective reduction reaction using lower amounts of the reducing agent requires that remaining reaction conditions are carefully selected as is provided by the present invention.

In one embodiment the amount of the reducing agent is at most 10 equivalents, such as at most 8, such at most 5 equivalents of the mixed di-sulfide, such as at most 4, such as at most 3, such as at most 2.5, such as at most 2, such as at most 1.5 equivalents of the mixed di-sulfide to be reduced.

In one embodiment the amount of the reducing agent is as 1-8, such as 2-6 equivalents of the mixed di-sulfide to be reduced.

The reduction of the mixed di-sulfide may, depending on the conditions, take minutes or hours. The skilled person will know that different conditions will result in different efficacy and thus the time and conditions needed to obtain complete or almost complete reduction of the mixed-di-sulfide are described in more details herein below.

The reducing agent may be added as concentrate or simply by adding the agent as a solid powder to the mixed di-sulfide composition. The reducing agent is mixed with the mixed di-sulfide composition to initiate reduction. The mix may be termed the reduction mix.

In order to have a sufficiently effective process the reduction should result in at least an 80% reduction, such as at least 90% reduction of the total amount of mixed disulfide. In such cases the reduction is considered satisfactory when the amount of the mixed di-sulfide is at most 20%, such as at most 10% of the amount of the mixed di-sulfide in the reduction mix. In preferred embodiments a reduction of around 95% of the mixed di-sulfide may be obtained leaving around 5% none reduced mixed di-sulfide in the solution comprising the reduced protein. In a further embodiment an efficient process leaves at most 2% mixed di-sulfide within a suitable time.

The reduction may occur during a period of at least 15 minutes, such as at least 30 minutes or such as at least 1 hour. In one embodiment the reduction mix is left for 2-10 hours, such as 3-6 hours or around 3-4 hours after addition of the reducing agent.

In one embodiment the reduction is performed for up to 24 hours, such as for up to 12 hours, such as for up to 8 hours, such as for up to 6 hours such as for up to 4 hours.

The reduction may in one embodiment take place at 1-50° C., such as at room temperature, such as at 18-25° C. In alternative embodiments the reduction may be performed at a colder temperature, such as below 10° C., such as around 4-6° C.

Depending on the conditions applied it may be advantageous to include salt in the reduction mix. The salt may be any salt or a combination of salts such as the salts described in relation to the mixed disulfide composition.

The inventors of the present invention have provided a series of conditions that allows for efficient reduction of the mix-disulfide and used this information to describe the concentration of the mixed di-sulfide to be used depending on temperature and salt (ionic strength of the reduction mix.

The amount of salt in a solution may be described by the ionic strength (I). This value is calculated from the concentrations and charges of all ions present in that solution. For simplicity any charge of the protein and the reducing agent is not included in the calculations according to the present invention, while buffer and salt components are. As seen in the examples herein increasing the ionic strength (mainly by increasing salt concentration) allows for an efficient reaction under less favourable conditions (low temp or lower concentration of reactants).

As described in Example 5 the conditions for the reduction reaction can be described using a correlation between the lowest suitable concentration of protein and the temperature and the ionic strength using a maximum of ten equivalents of reducing agent in the reduction mix. The minimum protein concentration that allows for efficient reduction is thus defined by the equation:

$$C_{min} = a * I^{-a_1} \exp(-b*T),$$

wherein T is the temperature in degrees Celsius, I is the ionic strength in M (mol/L), $C_{min}$ is M (mol/L) and the constants are $a=0.137*10^{-3} M^{1.425}$, $a_1=0.425$ and $b=0.070°$ $C.^{-1}$.

The upper limit for the concentration of the mixed di-sulfide may be of practical nature as many proteins are not soluble at very high concentrations. It is contemplated that for most proteins the reduction reaction will work at concentrations up to 100 g/L.

The upper limit for the ionic strength of the reduction mix may also be of practical nature as many salts are not soluble at very high concentrations. It is contemplated that for most salts the reduction reaction will work at concentrations up to 5 M.

The upper limit for the temperature of the reduction mix may be of practical nature as many proteins are not stable at very high temperature. It is contemplated that for most proteins the reduction reaction will work at concentrations up to 50° C.

Following this guidance an effective reduction reaction can be obtained using at most 10 equivalents of the reducing agent. It will also be clear to the skilled artisan that adjustment may be needed for individual proteins and reactions dependent on their stability.

In some embodiments the concentration of the mixed disulfide in the reduction mix is similar to the protein concentration of the mixed di-sulfide composition as the reducing agent is simply added to the composition in a concentrated form. In one embodiment the concentration of the mixed di-sulfide may be such as 5-4000 µM, 25-1000 µM, 50-850 µM, 100-600 µM, 250-600 µM or 250-500 µM. In further embodiments it is preferred that the concentration of the mixed di-sulfide is above 100 µM, such as 150 µM, 250 µM, 350 µM or even such as above 400 µM. In an embodiment where the mixed disulfide is a growth hormone or growth hormone variant the concentration is preferably 0.1-100 g/L, 0.5-25 g/L, 1-20 g/L, 2-15 g/L, 5-15 g/L or such as 5-12 g/L. In one embodiment the concentration of GH is at least 2.5 g/L, or such as at least 4.0 g/L, or such as at least 8.0 g/L or such as at least 10 g/L.

Intermediate step Before proceeding with the conjugation step the reduced protein (P-SH) may be separated from the reduction mix, such as from excess reducing agent and/or the small organic molecule of the mixed di-sulfide e.g. the H-S-Cap of the protein with a capped free cysteine (P-S-S-Cap). This optional step may be a step of removing molecules with a low molecular weight, such as molecules with a molecular weight below 10 kDa.

The skilled person will know of various methods for removing small molecular weight compounds, such as by filtration using a suitable membrane. In one embodiment the method comprises a step of diafiltration using a membrane/filter with a cut off of 5 kDa, 10 kDa or 30 kDa.

The cut-off can be chosen by the skilled person depending on the size specificity required; knowing that a cut-off close to the molecular weight of the product increases the risk of losing the product. A rule of thumb is to have a cut-off ⅓-⅙ the molecular weight of the product of interests.

A further option before proceeding with the conjugation step is to change the solution of the reduced protein (P-SH) e.g. to change the solvent, that is the individual excipients or the concentrations of the excipients of the solvent. In one embodiment the method comprises a step of changing solvent of the solution of step d) prior to step f).

A convenient way of changing the solvent is diafiltration. In one embodiment a diafiltration step is included to remove molecules of the solution with a molecular weight below 10 kDa and/or to change the solvent of the solution comprising the reduced protein (P-SH).

The efficacy of a diafiltration step e.g. the amount of small molecules and excipients which are removed, is related to the filtrate volume generated, relative to the retentate volume. It is also noted that the word "remove" in this context should be read as "reducing the concentration of" as residual amounts of low molecular weight molecules and excipients will usually be present after a diafiltration step (or an alternative process steps) "removing" molecules with a low molecular weight.

The total volume of the composition when diafiltration is started is used as reference for evaluating the volume needed. The diafiltration is usually performed with constant volume so that the volume of the generated filtrate equals the volume of the new solvent which is entered into the system. In order for the diafiltration to be effective more than one (1) volume of new solvent should preferably be used.

In one embodiment at least 2 volumes of solvent is applied for diafiltration, alternatively at least 3, such as at least 4 or at least 5 volumes of solvent is applied for the diafiltration.

In one embodiment the method according to the invention comprises a step of changing solvent of the solution comprising the reduced protein prior to initiating the conjugation reaction.

In one embodiment the method according to the invention comprises a step of changing solvent of the solution of step d) prior to step f). In a further embodiment the solvent is changed by diafiltration.

In one embodiment the solution of the reduced protein has or is changed to a solution with a pH suited for the protein, the reduced protein obtained and the protein conjugate to be prepared, such as a pH of 4-10, such as 5-9 or 6-8. In a further embodiment the pH may be 7.0-8.0, or 7.2-7.8 or 7.3-7.6 such as around 7.4-7.5.

In one embodiment the solution of the reduced protein has or is changed to a solution having a conductivity of around 1-150 mS/cm at 22° C., or such as 5-50 mS/cm at 22° C., or such as 5-25 mS/cm at 22° C. or conductivity around 10 mS/cm at 22° C.

In one embodiment the solution of the reduced protein comprising or is changed to a solution comprising a buffer. In one embodiment the buffer is selected from: BES, HEPES, MES, Phosphate, Citrate, Bis-Tris and triethanolamine.

In one embodiment the solution of the reduced protein comprises or is changed to a solution comprising 5-50 mmol/kg triethanolamine, such as 10-25 mmol/kg triethanolamine or such as around 20 mmol/kg triethanolamine.

In one embodiment the solution of the reduced protein comprises or is changed to a solution comprising a salt such as any of the salts described in relation to the mixed disulfide composition.

In one embodiment the solution of the reduced protein comprises or is changed to a solution comprising a salt selected from the group consisting of: Sodium Sulfate, Sodium Acetate, Ammonium Acetate, Guanidinium Hydrochloride, KI and NaCl.

In one embodiment the solution of the reduced protein comprises or is changed to a solution comprising NaCl.

In one embodiment the solution of the reduced protein comprises or is changed to a solution without salt. In one embodiment the solution of the reduced protein comprises or is changed to a solution without NaCl.

In one embodiment the solution of the reduced protein comprises or is changed to a solution comprising 10-2000 mmol/kg NaCl, such as 50-500 mmol/kg NaCl, such as 75-100 mmol/kg NaCl or such as around 80 mmol/kg NaCl.

The Conjugation Step

As described above the conjugation is according to the method performed by adding an activated chemical moiety (Z*) to the solution comprising the reduced protein.

If the prior reduction is not complete the ratio of reduced protein to mixed di-sulfide (P-SH/P-S-S-Cap) may prevent a high yielding conjugation reaction. Furthermore the presence of excess reduction agent and released Cap molecules may interfere with the conjugation reaction.

Again the relative ratio of the reactants e.g. the reduced protein and the activated chemical moiety influences the effectiveness of the reaction.

In one embodiment the molar concentration of the activated chemical moiety is at least equal or may be twice the molar concentration of the protein to be conjugated. This may also be expressed in equivalents e.g. at least 10, such as 8, such as 6, such as 4, such as 2 or such as at least one (1) equivalent(s) of the activated chemical moiety ($Z^*$) relative to the protein to be conjugated may be used. As the activated chemical moiety ($Z^*$) may be a costly resource it is advantageous to reduce the amount required, which as described herein is possible if the previous steps are optimized. An effective conjugation reaction using reduced amounts of the activated chemical moiety ($Z^*$) requires that remaining reaction conditions are carefully selected as is provided by the present invention. In one embodiment the amount of activated chemical moiety ($Z^*$) is at most 8 equivalents of the protein, such as at most 6, such as at most 4, such as at most 3, such as at most 2.5, such as at most 2, such as at most 1.5 equivalents of the protein to be conjugated.

As described in relation to the reduction mix, the solution of the conjugation may be termed a conjugation mix. With reference to the method steps a)-h) described above the addition of the activated chemical moiety ($Z^*$) in step f) leads to the formation of a conjugation mix. It is further clear that the components of the conjugation mix may be adjusted to optimize the conjugation conditions.

The conjugation of the reduced protein with the chemical moiety may, depending on the conditions, take minutes or hours. The skilled person will know that different conditions will result in different efficacy and thus the time needed to obtain complete or almost complete conjugation will vary based on the conditions as will be described more detailed herein below. According to the present method the conjugation reaction is considered satisfactory when the amount of the starting material e.g. the reduced protein reached 10%, such as 5% or preferably 2% or less.

As described in Example 6 the conditions for the conjugation reaction can be described using a correlation between the lowest suitable concentration of protein dependent on the temperature, the ionic strength, and the relative amount of activated chemical moiety ($Z^*$) to be used in the conjugation mix. The minimum protein concentration ($C_{min}$ in M (mol/L) that allows for efficient conjugation is thus defined by $C_{min}=a^*\exp(-b_1^*T-b_2^*I)+d^*\exp(-d_1^*T)$, wherein T is the temperature in degrees Celsius, I is the ionic strength in M (mol/L), $a=6.96^*10^{-4}$ M, $b1=0.0396°$ $C.^{-1}$, $b2=10.9$ $M^{-1}$, $d=6.12^*10^{-5}$ M and $d1=0.0289°$ $C.^{-1}$.

As described above in relation to the reduction the upper limit for the protein, ionic strength and temperature may be of practical nature. It is contemplated that for most proteins the conjugation reaction will work at concentrations up to 100 g/L. It is likewise contemplated that for most salts the conjugation reaction will work at concentrations up to 5 M. It is further contemplated that for most proteins the conjugation reaction will work at concentrations up to 50° C. Following this guidance an effective conjugation reaction can be obtained using at most 4 equivalents of the activated chemical moiety ($Z^*$).

The activated chemical moiety may be added as concentrate or simply by adding the agent as a solid powder to the solution comprising the reduced protein. In one embodiment the activated chemical moiety is dissolved in a suitable solution prior to adding the activated chemical moiety to the solution comprising the reduced protein. It may also be that the chemical moiety is activated in a solution prior to the conjugation reaction.

According to the invention the conjugation mix preferable has a pH of 5-10, such as 7.0-9.0 or 7.0-8.5.

In one embodiment the concentration of the reduced protein in the conjugation mix is at least 50 µM. In further embodiments it is preferred that the concentration of the reduced protein in the conjugation mix is above 100 µM, such as 150 µM, 250 µM, 350 µM or even such as above 400 µM.

In an embodiment for conjugation of human growth hormone the concentration is at least 1 g/L. In preferred embodiments the concentration of human growth hormone is even higher such as at least 2.0 g/L, such as at least 3.0 g/L, such as at least 5 g/L, or at least 7.5 g/L or at least 10 g/L.

According to the present invention efficiency of the conjugation can be improved by included salt in the conjugation mix. This is particular helpful in the lower protein concentration range e.g. when the concentration of the reduced protein is 50 mM-150 mM or for human growth hormone when the protein concentration is 1-3 g/L in the conjugation mix. It is of course also possible to include salt when a higher protein concentration is applied.

Salt may be included in either of the solutions used in the conjugation mix or added separately to optimize reaction conditions. Salts are made up by a cation and an anion providing an equal positive and negative charge. Salts may be described as being neutral, basic or acidic based on the ions obtained when hydrolysed in water. The salts may be any salt, such as any of the salts described in relation to the mixed disulfide composition. Salts may be inorganic or organic such as Sodium, Ammonium, Guanidinium, and Potassium salts, or such as Sulfate, Acetate, and Halogenide salts, or such as Sodium Sulfate, Sodium Acetate, Ammonium Acetate, Guanidinium Hydrochloride, KI, and NaCl.

The amount of salt in a solution may be described by the ionic strength (I). This value is calculated from the concentrations and charge of all ions present in that solution. For simplicity any charge of the protein and the activated chemical moiety ($Z^*$) is not included in the calculations according to the present invention, while buffer and salt components are. As seen in the examples herein the concentration of Triethanolamine (buffer) and NaCl (or other salts) are included when I is calculated.

In one embodiment the Ionic strength (I) of the conjugation mix is above 0.1 M, such as above 0.2 M, such as above 0.3 M, such as above 0.4 M, such as above 0.5 M. As mentioned above this may be particular useful in cases where the concentration of the reduced protein in the conjugation mix is low such as from 50-250 µM or such as 1-5 g/L or 0.5-3.0 g/L for human growth hormone.

In a similar way, the reaction conditions may be adjusted depending on the temperature for the conjugation reaction. In many situations it is considered advantageous to perform large scale reactions at or around room temperature (T=18-25 C), but in other situations it may for various reasons be preferred to either increase or decrease the temperature for the conjugation reaction.

In one embodiment the conjugation reaction is performed at 15-50 C, such as in situations where the concentration of the reduced protein is above 150 µM as describe above. In alternative embodiments a lower temperature range can be applied if salt is included in the conjugation mix.

In on embodiment where the conjugation reaction is performed at a temperature below room temperature, such as below 20 C, such as below 15 C, such as below 10 C, or such as at 2-8 C, the conjugation mix preferably has a Ionic strength (I) above 0.1 M, such as above 0.2 M, such as above 0.3 M, such as above 0.4 M, such as above 0.5 M.

The activated chemical moiety is mixed with the reduced protein to initiate conjugation. The mix is herein termed the conjugation mix. The conjugation may occur during a period of at least 15 minutes, such as at least 1 hour, such as at least 2 hours, such as at least 3 hours, such as at least 4 hours or such as at least 5 hours. In one embodiment the conjugation mix is left for 2-hours, such as 3-6 hours or around 3-4 hours after addition of the activated chemical moiety. In one embodiment the conjugation mix is left for 2-20 hours, such as 6-16 hours or around 8-12 hours after addition of the activated chemical moiety.

In one embodiment the conjugation may be performed for up to 24 hours, such as for up to 18 hours, such as for up to 12 hours, such as for up to 6 hours, such as for up to 4 hours.

The conjugation reaction may take place at various temperatures such as from 1-50° C., or such as from 10-50° C. The conjugation may in one embodiment take place at room temperature, such as at 15-25° C. or 20-25° C. In alternative embodiments the reduction may be performed at a colder temperature, such as below 10° C., such as around 4-6° C.

As the conjugation reaction progresses a preparation of the conjugated protein (P-S-Z) is obtained and once such a preparation is obtained the skilled person may proceed with further purification steps, such as diafiltration of the product into a suitable storage buffering removing impurities with a low molecular weight as described above or with more specific purification steps such as anion exchange chromatography.

Equipment

The equipment used in the examples herein exemplifies suitable equipment for performing the method. The method may be performed in ordinary glasses/tubes or the like with intervening transfers as required. The invention may also with high advantageousness be performed in cross flow filtration or tangential flow filtration (TFF) equipment. Such equipment is well known in the art and allows for up-scaling of the process from lab to industry scale In cross-flow filtration the liquid is passed tangentially across the membrane/filter and the retentate and the permeate or filtrate can be continuously collected/drained and the retentate may be re-circulated in the system.

As described in the examples the system can be used for ultra- and/or diafiltration of the protein at various stages in the conjugation process. Prior to reduction the di-sulfide preparation may be ultra-filtrated to obtain a composition of a mixed di-sulfide of a desired concentration.

The inlet pressure and outlet pressure may be adjusted and new solutions including buffers and/or other excipients may be added as the permeate is drained from the system. The system can also be used without applying a pressure difference meaning that liquid volume is constant and no permeate is drained from the system.

With reference to the method of the invention one or more of the step(s) is/are in an embodiment performed in an ultrafiltration/diafiltration system or TFF system.

In a further embodiment the reduction (step c) is performed in a retentate tank of an ultrafiltration/diafiltration system or cross flow filtration/TFF system.

The reducing agent may be added to the retentate tank and circulation applied to mix the reducing agent with the composition of the mixed di-sulfide. During mixing the excipients of the solution (comprising the mixed di-sulfide and the reducing agent) is not changed and the volume hereof is held constant. Although the mixing occurs in the system no filtration is applied e.g. no additional solution is entered into the system and/or no pressure difference is applied across the membrane and consequently no permeate is obtained.

In one embodiment no permeate is obtained or produced during adding and/or mixing the reducing agent with the mixed di-sulfide. In one embodiment no permeate is obtained or produced during the reduction step. In one embodiment dia-filtration is not performed as part of step b) and/or c).

In a further embodiment the conjugation (step g) is performed in a retentate tank of an ultrafiltration/diafiltration system or cross flow filtration/TFF system.

In an embodiment a cross flow filtration/tangential flow filtration system is used throughout the process.

In a further embodiment the method includes one or more ultrafiltration/diafiltration step(s) to concentrate the protein, to remove molecules with a molecular weight below 10 kDa or to change the excipients or concentration of excipients of the solutions used.

As the method has come to an end, the preparation of the conjugated protein (P-S-Z) (step h) can be obtained by emptying the cross flow filtration system.

Embodiments and examples described here below describes and illustrates certain features of the invention, it is anyway to be understood, that the invention is not limited hereto as many modifications, substitutions, changes, and equivalents will now occur to those of ordinary skill in the art, and thus also considered part of the invention.

EMBODIMENTS

1. A method for preparing a protein conjugate wherein the protein (P) is covalently bound to a chemical moiety (Z) via a thioether, comprising the steps of;
   a) obtaining a composition of a mixed di-sulfide comprising the protein,
   b) adding a reducing agent to said protein composition obtaining a reduction mix,
   c) allowing reduction to occur,
   d) obtaining a solution comprising a reduced protein (P-SH),
   e) optionally removing molecules of the solution with a molecular weight below 10 kDa,
   f) adding an activated chemical moiety (Z*) to the solution comprising the reduced protein obtaining a conjugation mix,
   g) allowing a conjugation reaction to occur and
   h) obtaining a preparation of said conjugated protein (P-S-Z).

2. The method according to embodiment 1, wherein the method is performed in a cross flow filtration/tangential flow filtration system.

3. The method according to any of the previous embodiments, wherein the mixed di-sulfide is a protein with a capped free cysteine (P-S-S-Cap).

4. The method according to embodiment 3, wherein the composition of a) has a concentration of P-S-S-Cap of at least 100 µM, such as 150 µM, 250 µM, 350 µM or even such as above 400 µM.

5. The method according to embodiment 3, wherein the composition of a) has been obtained by ultra-filtration.

6. The method according to embodiment 3, wherein the Cap is derived from cysteine, cysteamine or glutathione.

7. The method according to any of the previous embodiments, wherein the conjugation of step g) is a selective chemical conjugation.
8. The method according to any of the previous embodiments, wherein the reducing agent is a phosphine, such as an aromatic phosphine, such as triarylphosphine, such as a substituted triarylphosphine, such as trisodium triphenylphosphine-3,3',3"-trisulfonate (TPPTS) or such as disodium triphenylphosphine-3,3'-disulfonate (TPPDS).
9. The method according to any of the previous embodiments, wherein the amount of the reducing agent is at least 2 equivalents of the protein such as 4-15 equivalents, such as around 5-10 equivalents or the protein.
10. The method according to any of the previous embodiments, wherein the reduction is performed for less than 10 hours.
11. The method according to any of the previous embodiments, wherein the chemical moiety (Z) is a property-modifying group such as protracting agent.
12. The method according to any of the previous embodiments, wherein the activated chemical moiety (Z*) is a halogenated protracting agent
13. The method according to any of the previous embodiments, wherein the activated chemical moiety (Z*) is a maleimide substituted protracting agent.
14. The method according to any of the previous embodiments, wherein the chemical moiety (Z) is an albumin binder (AB).
15. The method according to any of the previous embodiments, wherein the activated chemical moiety (Z*) is a halogenated albumin binder, wherein said halogene is Br, I or Cl.
16. The method according to any of the previous embodiments, wherein the activated chemical moiety (Z*) is a maleimide substituted albumin binder (AB).
17. The method according to any of the previous embodiments, wherein at most 5, such as at most 4, 3 or at most 2 equivalents of the activated chemical moiety (Z*), relative to the mixed disulfide, is added in step f).
18. The method according to any of the previous embodiments, comprising a step of changing solvent of the solution of step d) prior to step f).
19. The method according to any of the previous embodiments, comprising step e).
20. The method according to any of the previous embodiments, wherein step e) and/or the solvent change step is performed by diafiltration.
21. The method according to any of the previous embodiments, comprising a further step i) removing molecules with a molecular weight below 10 kDa and/or changing solvent of the preparation of step h).
22. The method according to any of the previous embodiments, comprising a further step i) performed by diafiltration of the preparation of step h).
23. The method according to any of the previous embodiments, wherein one or more of the composition of step a), the solution of step d) and/or the preparation of step h) includes a buffer and a salt.
24. The method according to any of the previous embodiments, wherein the reduction mix of step b) includes a buffer and a salt.
25. The method according to any of the previous embodiments, wherein the conjugation mix of preparation of step f) includes a buffer and a salt.
26. The method according to any of the previous embodiments, wherein step i) removes salt.
27. The method according to any of the previous embodiments, wherein the buffer is triethanolamine.
28. The method according to any of the previous embodiments, wherein the salt is NaCl and/or KI.
29. The method according to any of the previous embodiments, wherein the composition of step a), the solution of step d) and the preparation of step h) have the same pH.
30. The method according to any of the previous embodiments, wherein the composition of step a), the solution of step d) and the preparation of step h) have pH 7.0-8.0.
31. The method according to any of the previous embodiments, wherein the solution of step d) and the preparation of step i) have different conductivity.
32. The method according to any of the previous embodiments, wherein the conductivity of the solution of step d) is 10 mS/cm (22° C.).
33. The method according to any of the previous embodiments, wherein the conductivity of the preparation of step i) is 1-2 mS/cm (22° C.).
34. The method according to any of the previous embodiments, wherein step e) is performed using a cellulose membrane, such as a 10 kD Hydrosart© membrane.
35. The method according to any of the previous embodiments, wherein step i) is performed using a cellulose membrane, such as a 10 kD Hydrosart© membrane.
36. The method according to any of the previous embodiments, wherein at least one step is performed in a cross flow filtration/tangential flow filtration system.
37. The method according to any of the previous embodiments, wherein the reduction (step c) is performed in a retentate tank of ultrafiltration/diafiltration equipment.
38. The method according to any one of the previous embodiments, wherein the conjugation (step g) is performed in a retentate tank of ultrafiltration/diafiltration equipment.
39. The method according to any of the previous embodiments, wherein a cross flow filtration/tangential flow filtration system is used throughout the process.
40. The method according to any of the previous embodiments, wherein the preparation h) or i) is obtained by emptying the cross flow filtration system.
41. The method according to any of the previous embodiments, wherein the preparation h) or i) has a concentration of at least 5 g/L.
42. The method according to any of the previous embodiments, wherein the conjugated protein (P-S-Z) of preparation h) or i) is purified by an-ion exchange chromatography (AIEC) using such as Q sepharose HP.
43. The method according to any of the previous embodiments, wherein the conjugated protein (P-S-Z) of preparation h) or i) is concentrated using ultrafiltration resulting in a concentration of at least 10 g/L, such as 20 g/L.
44. The method according to any of the previous embodiments, wherein the free cysteine is introduced by a point mutation.
45. The method according to any of the previous embodiments, wherein the protein is a growth hormone polypeptide.
46. The method according to any of the previous embodiments, wherein the free cysteine of the growth hormone polypeptide is provided by a point mutation selected from the group consisting of: E30C, Y42C, S55C, S57C, S62C, Q69C, S95C, A98C, N99C, L101C, V102C and S108C.
47. The method according to any of the previous embodiments, wherein the growth hormone polypeptide comprise a L101C point mutation.

48. The method according to any of the previous embodiments, wherein the reduction mix of step b) has a concentration of the mixed disulfide of at least $C_{min}$, wherein $C_{min}$ is defined by:

$$C_{min}=a*I^{-a_1}\exp(-b*T),$$

wherein T is the temperature in degrees Celsius, I is ionic strength (M) of the reduction mix, $a=0.137*10^{-3}$ $M^{1.425}$, $a_1=0.425$ and $b=0.070°\ C.^{-1}$.

49. The method according to any of the previous claims, wherein the conjugation mix of f) has a concentration of the reduced protein of at least $C_{min}$, where $C_{min}$ is defined by:

$$C_{min}=a*\exp(-b_1*T-b_2*I)+d*\exp(-d_1*T)$$

wherein T is the temperature in degrees Celsius, I is the ionic strength (M) of the conjugation mix, $a=6.96*10-4$ M, $b1=0.0396°\ C.^{-1}$, $b2=10.9\ M^{-1}$, $d=6.12*10^{-5}$ M and $d1=0.0289°\ C.^{-1}$.

EXAMPLES

General Method for Preparing a Growth Hormone Protein with a Free Cystein

The protein may be expressed recombinantly in *E. Coli* such as described in WO 2011/089255.

In short, *E. coli* cells expressing GH-L101C are isolated by centrifugation. The cell pellet is resuspended in a Tris buffer containing EDTA and Polysorbate 20. Cells are disrupted by passing through a high pressure homogeniser. The obtained homogenate is mixed with urea solution, pH adjusted and left overnight. The protein is hereby solubilised and naturally occurring glutathione is coupled to the free cysteine leading to formation of GH-L101C-S-Glutathion. Prior to reduction/conjugation with the albumin side chain the GH-L101C-S-Glutathion precursor may be purified by anion exchange chromatography.

The protein is captured in an anion exchange step using Q Sepharose XL as stationary phase and Tris buffer as the mobile phase. Elution is performed using a linear sodium chloride gradient. After an adjustment of the ionic strength, the eluted protein is purified by hydrophobic interaction chromatography. Phenyl Sepharose FF is used as stationary phase and Tris buffer as the mobile phase. Elution is performed by applying a step gradient where sodium chloride concentrations are varied.

The MEAE tag is removed by enzymatic digestion of the precursor, resulting in GH-L101C-S-Glutathion which is finally purified by anion exchange after dilution. Source 30Q is used as stationary phase and triethanol amine as the mobile phase. Elution is performed using a linear sodium chloride gradient. The protein is now ready for the conjugation step.

General Method for Preparing an Albumin Binder Side Chain

The albumin binder side chain may be synthesised as described in WO 2011/089255.

Prior to conjugation of the albumin binder side chain to the GH-L101C-SH the side chain is activated by dissolving the side chain in a solution of KI (5M), ascorbic acid (50 mM) and triethanolamine (150 mM), pH 7.5. The concentration of the side chain in the KI solution is usually between 5 and 30 g/L.

Example 1

Reduction and Conjugation without the Use of a TFF System

GH-L101C-S-Glutathion is used as obtained from anion exchange chromatography as described above. The concentration is 2.4 g/L, NaCl is 0.08 M, triethanol amine is 0.02 M and pH 7.4. The ionic strength is 0.09 M.

TPPDS (5 equivalents ~0.12 g per g GH-L101C-S-Glutathion) is added to the GH-L101C-S-Glutathion and the reduction is followed by AIE-HPLC every 30 minutes for 4 hours (using an auto-sampler, see FIG. 1A). After 4 hours the side chain solution (2.2 equivalents 0.12 g per g GH-L101C-S-Glutathion) is added to the reduction mixture and the conjugation reaction is followed by AIE-HPLC over night (see FIG. 1B).

Example 2

Reduction and Conjugation of GH-L101C-SH with the Use of a TFF System for Ultrafiltration and Diafiltration Equipment:
Millipore Labscale TFF system
ÄKTAcrossflow TFF system
Sartocon Slice 200 Filter, cut off 10 kD (Hydrosart©)
Solutions:

|  | GH-L101C-S-Glutathion prep: | Diafiltration buffer "1" | Diafiltration buffer "2" |
| --- | --- | --- | --- |
| Triethanolamine (mmol/kg) | 20 | 20 | 20 |
| NaCl (mmol/kg) | 80 | 80 | 0 |
| pH (22° C.) | 7.4 | 8.0 | 8.0 |
| Conductivity (mS/cm) | 10 | 10 | 1-2 |
| Ionic strength (M) | 0.09 | 0.09 | 0.01 |

Figure 2:
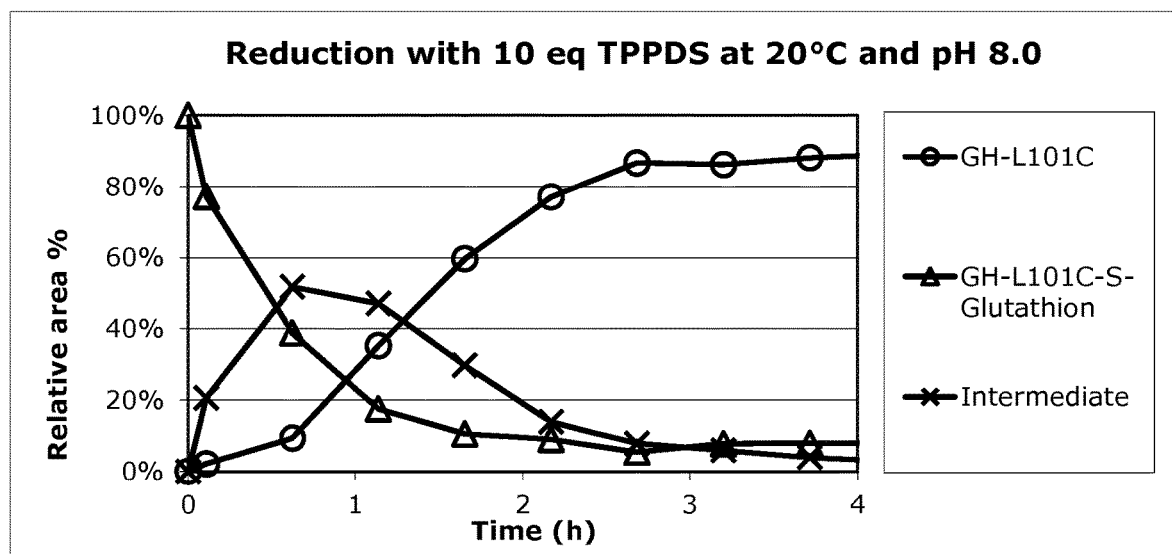
FIG. 2 shows the reduction of GH-L101C-S-Glutathion after ultrafiltration to 5 g/L with 10 equivalents of TPPDS at pH 8.0 and 20° C. The reaction was followed by AIE-HPLC, and the relative area % of the starting material, reaction intermediate and product is plotted versus reaction time. Δ: GH-L101C-S-Glutathion, X: reaction intermediate, ○: GH-L101C-SH. The figure represents data from experiment 17 of Table 1.

A preparation of GH-L101C-S-Glutathion is obtained as described in the method above. The GH preparation is loaded in the TFF system (Millipore Lab scale TFF System) and ultrafiltration is performed until a concentration of 5 g/L is obtained. The reducing agent (TPPDS) is added in excess of GH (10 equivalents ~0.24 g per g GH-L101C-S-Glutathion) into the retentate tank and circulation is applied until homogenous (approximately 15 minutes). The reduction mix is left (without circulation) for 4 hours. The reaction is followed by AIE-HPLC. As can be seen in FIG. 2, the reduction occurs with-in 4 hours under the applied conditions.

In order to evaluate the effect of including a diafiltration step samples (1 mL) of the reduced GH-L101C-SH is obtained before and after such a step and separate conjugation reactions are performed.

The reduced protein is diafiltered with 5 times the volume at constant volume using diafiltration buffer 1 (conditions: 350 mL, 0.4 bar (in), 0.3 bar (out) and a flux of 17 LMH) using a 10 kD (Hydrosart©) membrane to remove low molecular weight (<10 kda) molecules. OD280 of the reduction solution was 23.7 due to TPPDS. The removal of TPPDS was followed at OD280 and the permeate initially showed a high absorbance at 280 nM decreasing to 0.058. At the end the retentate had an OD280 equivalent to the OD280 before addition of TPPDS indicating that TPPDS had been removed.

Figure 3:
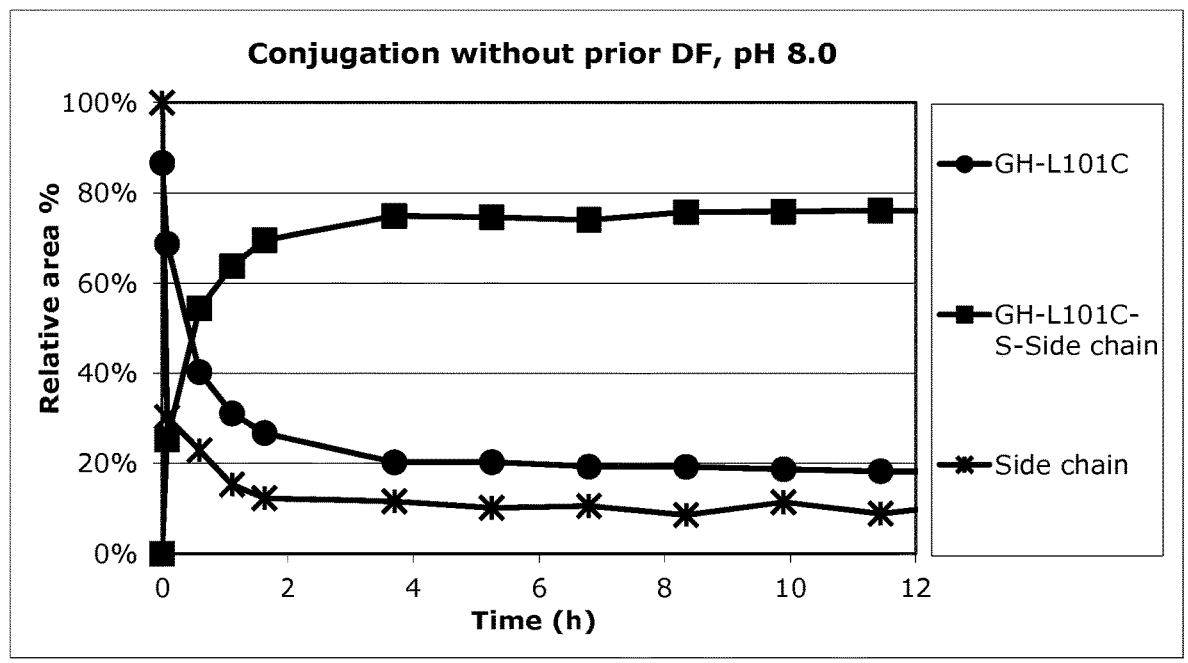
FIG. 3A shows the conjugation of side chain with the reduced GH-L101C-SH after reduction for 4 hours as shown in FIG. 2. Three (3) equivalents of side chain are added directly to the reduction mix without any diafiltration. The relative area % of the starting material and product is plotted versus reaction time. Area % of side chain is set to 100% at beginning of conjugation reaction. ✳: Side chain, ●: GH-L101C-SH, ■: GH-L101C-S-Side chain.
FIG. 3B shows the conjugation of side chain with the reduced GH-L101C-SH after reduction for 4 hours as shown in FIG. 2. Three (3) equivalents of side chain are added to the reduced protein after the reduction mix has been diafiltered into buffer 1. The relative area % of the starting material and product is plotted versus reaction time. Area % of side chain is set to 100% at beginning of conjugation reaction. ✳: Side chain, ○: GH-L101C-SH, □: GH-L101C-S-Side chain.
Figure 3:
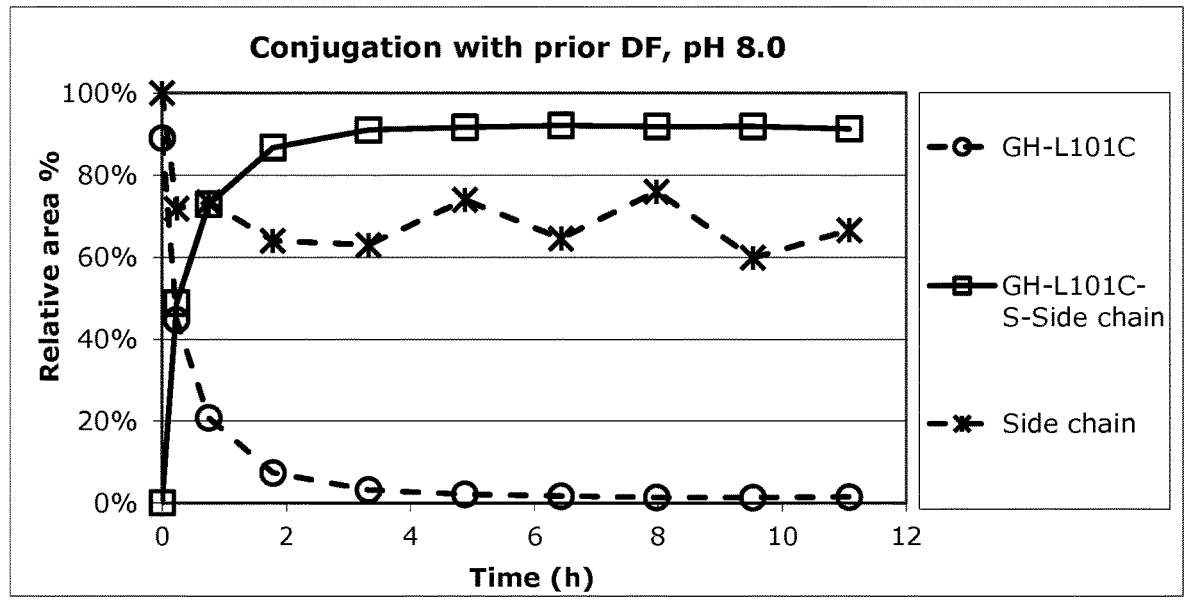

Conjugation is performed using 1 mL of the reduced protein (obtained before diafiltration) by addition of 0.1 mL side chain solution corresponding to the addition of 3 equivalents (~0.16 g per g GH-L101C-S-Glutathion) of side chain, and the alkylation process is monitored by AIE-HPLC (FIG. 3A).

In parallel a conjugation reaction is set up using 1 mL of the concentrated retentate (reduced GH-L101C-SH after diafiltration) and adding 0.1 mL side chain solution corresponding to the addition of 3 equivalents (~0.16 g per g GH-L101C-S-Glutathion) of side chain. The conjugation reaction is monitored by HPCL (FIG. 3B).

The remaining concentrated retentate (66 mL) is mixed with side chain solution and circulated in the TFF system to ensure mixing. The mixture is left over night without pumping.

To further purify the product, the conjugation mix (retentate) is diafiltered with 5 times the volume at constant volume into diafiltration buffer 2 removing molecules of the solution with a molecular weight below 10 kDa and preparing the product for any subsequent chromatographic step.

AIE-HPLC of the final diafiltered conjugated GH-L101C-S-Side chain shows an almost complete conversion of GH-L101C-SH and a successful reduction in the amount of side chain and KI compared to the conjugation mix (not shown).

Example 3

Reduction and Conjugation of GH-L101C-SH with the Use of a TFF System for Ultrafiltration and Diafiltration with High GH Concentration and Low Side Chain Concentration Equipment:
Millipore Labscale TFF system
ÄKTAcrossflow TFF system
Sartocon Slice 200 Filter, cut off 10 kD (Hydrosart©)
Solutions:

|  | GH-L101C-S-Glutathion prep: | Diafiltration buffer "3" | Diafiltration buffer "4" |
|---|---|---|---|
| Triethanolamine (mmol/kg) | 20 | 20 | 20 |
| NaCl (mmol/kg) | 80 | 80 | 0 |
| pH (22° C.) | 7.4 | 7.4 | 7.4 |
| Conductivity (mS/cm) | 10 | 10 | 1-2 |
| Ionic strength (M) | 0.09 | 0.09 | 0.01 |

As above a GH preparation is loaded in the TFF system (ÄKTAcrossflow) and ultrafiltration is performed until a concentration of GH-L101C-S-Glutathion of 10 g/L is obtained (inlet pressure 2 bar, outlet pressure 1 bar). The same amount of TPPDS (5 eq), as in example 1, is added to the retentate tank and circulation is applied until homogenous (approximately 15 minutes). The reduction is followed by AIE-HPLC every 30 minutes for 4 hours (using an auto-sampler, see FIG. 4A).

After 4 hours the reduction mix is diafiltered 5 times at constant volume into diafiltration buffer 3. The side chain solution (2.2 equivalents ~0.12 g per g GH-L101C-S-Glutathion) is added and circulation is applied until homogenous (approximately 15 minutes). The conjugation reaction is followed by AIE-HPLC (using an auto-sampler, see FIG. 4B).

After the conjugation reaction the conjugation mix is diafiltered with 5 times the volume into diafiltration buffer 4 in order to reduce the content of KI and remaining side chain and prepare the conjugated protein for any subsequent chromatographic step.

Example 4

Method for Purifying the Conjugated Protein GH-L101C-S-Side Chain

After conjugation the product may by purified by anion exchange chromatography, wherein Q Sepharose HP is used as stationary phase and triethanol amine as the mobile phase. Elution may be performed as a linear sodium chloride gradient. The product may be subjected to diafiltration into suitable storage buffer removing impurities with a size smaller than the cut-off of the 10 kDa membrane. A UF/DF-step also allows for preparation of a concentrated product.

Summary of Example 1-4

Figure 4:
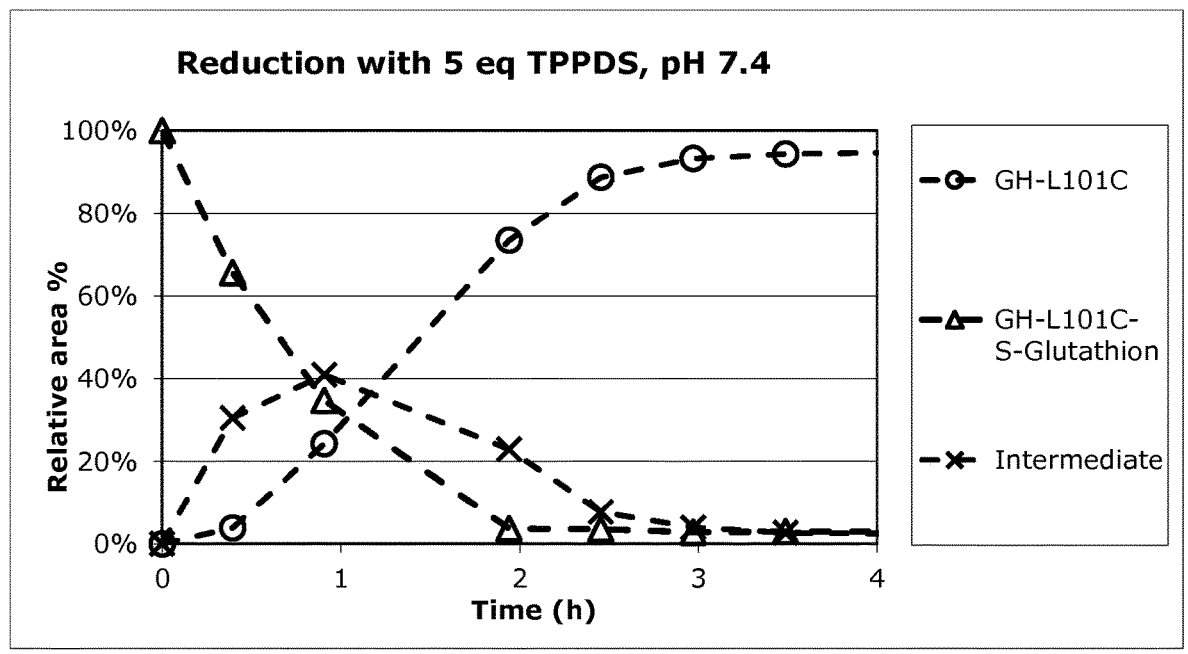
FIG. 4A shows the reduction of GH-L101C-S-Glutathion after ultrafiltration to a concentration of 10 g/L with 5 equivalents of TPPDS at pH 7.4. The reaction was followed by AIE-HPLC, and the relative area % of the starting material, reaction intermediate and product is plotted versus reaction time. Δ: GH-L101C-S-Glutathion, X: reaction intermediate, ○: GH-L101C-SH.
FIG. 4B shows the conjugation of side chain with the reduced GH-L101C-SH after reduction for 4 hours as shown in FIG. 4A. 2.2 equivalents of side chain are added to the reduced protein after the reduction mix has been diafiltered into buffer 3. The relative area % of the starting material and product is plotted versus reaction time. Area % of side chain is set to 100% at beginning of conjugation reaction. X: Side chain, ○: GH-L101C-SH, Δ: GH-L101C-S-Side chain.
Figure 4:
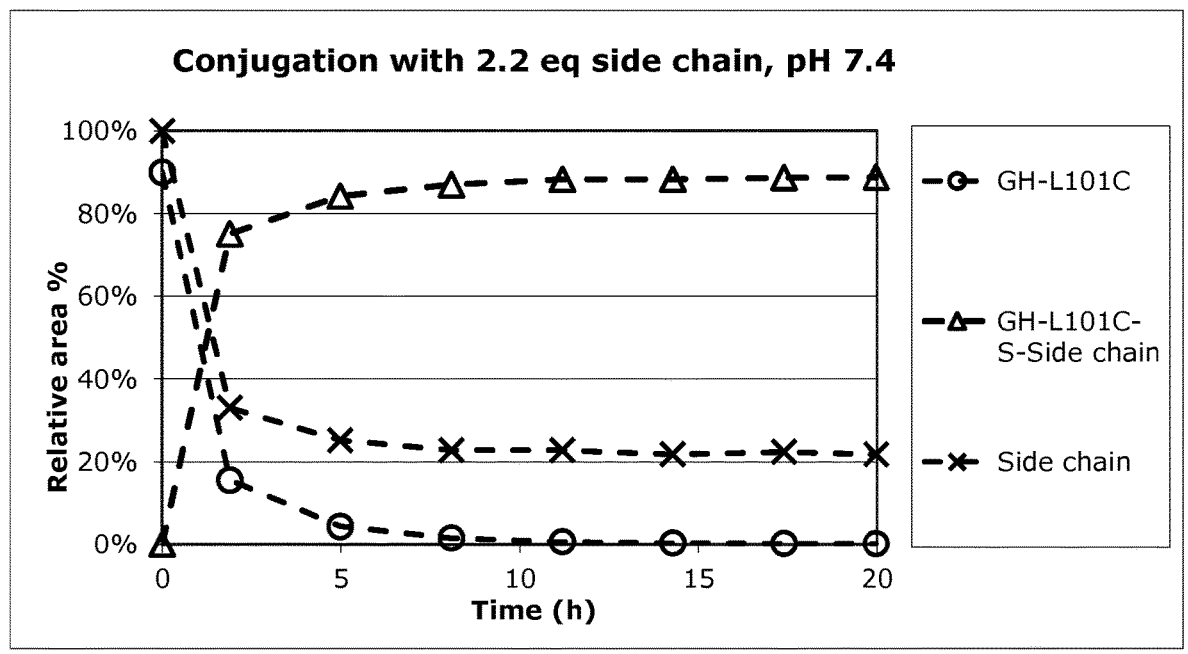

The reduction and conjugation processes as performed using a TFF system have proven successful. 3 examples of the reduction of GH-L101C-S-Glutathion with the use of TPPDS have been presented and the results are shown in FIGS. 1A, 2 and 4A. FIG. 1A shows the reduction with 5 equivalents of TPPDS at a protein concentration of 2.4 g/L. The conversion of the starting material is only approximately 60% after 4 hours. However, when the reduction is performed at 5 g/L with 10 equivalents of TPPDS (FIG. 2) or at 10 g/L with 5 equivalents of TPPDS (FIG. 4A) the reaction is completed within less than 4 hours. It is also observed that the amount of reduction agent can be reduced when the substrate (protein precursor) concentration is higher.

The above examples include several demonstrations that the conjugation reaction can be performed in a TFF system (FIGS. 3A, 3B and 4B). In all the examples the reduction was allowed to run for 4 hours.

The conjugation shown in FIG. 1B resulted in conjugation of less than 60% after 20 hours. As seen in FIG. 1A, the reduction of the starting material was incomplete and therefore the remaining GH-L101C-S-Glutathion and reaction intermediate could interfere with the conjugation reaction. During the reaction period GH-L101C-S-Glutathion and reaction intermediate were completely converted to GH-L101C-SH but a complete conversion to GH-L101C-S-side chain did not occur. It is possible that the side chain was depleted by reaction with Glutathion and possibly the remaining TPPDS, before it could react with the free thiol of the protein.

The only difference between FIGS. 3A and 3B is an intermediate diafiltration step which increases the yield of the conjugation to above 90% compared to below 80%.

It is also noted that the intermediate diafiltration affects the concentration of the side chain. Without diafiltration the concentration of the side chain drops almost immediately, while the performance of an intermediate diafiltration steps avoids this dramatic drop in side chain concentration.

It is likely that the drop in side chain concentration is caused by reaction of the side chain with released glutathione (corresponding to 1 equivalent of side chain) and possibly TPPDS. By introducing the intermediate diafiltration these side reactions are no longer possible.

Another advantage of the combined ultrafiltration and diafiltration is illustrated when comparing FIGS. 3B and 4B. In FIG. 3B the fast and almost complete conjugation reaction is obtained by the addition of 3 equivalents of side chain and using pH 8.0. Since the protein is not very stable at pH 8.0 a lower pH would be of an advantage. However a lower pH will also result in a lower reaction rate. Similarly the use of side chain should be limited to a minimum but a decrease in side chain will also decrease the reaction rate. FIG. 4B shows that it is possible to obtain a fast and satisfactory reaction with the use of less side chain and a lower pH by increasing the protein concentration during the conjugation reaction.

As the conjugated protein as obtained in the conjugation mix is not very stable it may be advantageous to include a further purification step. As described in example 4 the introduction of a final diafiltration step results in a stable protein preparation which can be stored under normal conditions and additionally the protein preparation can be applied directly to a subsequent column without dilution or pH adjustment thus avoiding further handling.

Example 5

Defining Minimum Protein Concentration for the Reduction Reaction

The inventors of the present inventions have found that a key parameter to control is the concentration of the protein in the reduction reaction mixture. As seen above, in situations where the starting material has a relatively low concentration an improved reaction can be obtained by including a concentration step before adding the reduction agent. By concentrating the protein composition a satisfactory reduction could be obtained using fewer equivalents of reducing agent. Further studies showed that the reaction rate was also influenced by the temperature and the ionic strength of the reduction mix.

In order to describe the combined effect of the protein concentration, the temperature, and the ionic strength of the reduction mix a significant number of conditions were investigated (examples in table 1). As standard, Triethanolamine (20 mM) and NaCl (80 mM) was included providing a ionic strength of 0.09. In Exp. 4, 5, 10, 11 and 16 additional salt was included to raise the ionic strength, while the salt concentration was reduced in 14 and 15. The ionic strength for the buffer is calculated as the fraction of charged buffer multiplied by the total concentration of buffer. The fraction (x) of charged buffer is calculated from the pKa of the buffer using the Henderson-Hasselbalch equation:

$$x = \frac{1}{1 + 10^{pH-pKa}} m.$$

pKa is 7.8 at 22° C. for triethanol amine.

TABLE 1

The conditions for the reduction reactions including protein concentration (Cp), Temperature (Temp), the number of equivalents (n) of reduction agent, and ionic strength in the reduction mix (including buffers but excluding protein component) for reduction experiments 1-20. The calculated $C_{min}$ as described below is also included for comparison. Examples 9-20 are plotted in FIG. 5.

| Exp. | $C_P$ (mM) | Temp (° C.) | n (TPPDS) | NaCl (mM) | Triethanol-amine (mM) | Ionic strength (M) | pH | $C_{min}$ (mM) |
|---|---|---|---|---|---|---|---|---|
| 1 | 0.11 | 30 | 5 | 80 | 20 | 0.09 | 7.5 | 0.05 |
| 2 | 0.11 | 30 | 10 | 80 | 20 | 0.09 | 7.5 | 0.05 |
| 3 | 0.45 | 20 | 3 | 80 | 20 | 0.09 | 7.4 | 0.09 |
| 4 | 0.45 | 20 | 3 | 580 | 20 | 0.59 | 7.4 | 0.04 |
| 5 | 0.22 | 20 | 5 | 580 | 20 | 0.59 | 7.4 | 0.04 |
| 6 | 0.22 | 20 | 5 | 80 | 20 | 0.09 | 7.4 | 0.09 |
| 7 | 0.10 | 20 | 5 | 80 | 20 | 0.09 | 7.4 | 0.09 |
| 8 | 0.11 | 20 | 5 | 80 | 20 | 0.09 | 7.5 | 0.09 |
| 9 | 0.11 | 5 | 10 | 80 | 20 | 0.09 | 7.4 | 0.26 |
| 10 | 0.11 | 5 | 10 | 280 | 20 | 0.29 | 7.4 | 0.16 |
| 11 | 0.11 | 5 | 10 | 580 | 20 | 0.59 | 7.4 | 0.12 |
| 12 | 0.45 | 5 | 10 | 80 | 20 | 0.09 | 7.4 | 0.26 |
| 13 | 0.04 | 40 | 10 | 80 | 20 | 0.09 | 7.4 | 0.02 |
| 14 | 0.04 | 40 | 10 | 27 | 7 | 0.03 | 7.4 | 0.04 |
| 15 | 0.02 | 40 | 10 | 16 | 4 | 0.02 | 7.4 | 0.04 |
| 16 | 0.02 | 40 | 10 | 516 | 4 | 0.52 | 7.4 | 0.01 |
| 17 | 0.22 | 20 | 10 | 80 | 20 | 0.09 | 8 | 0.09 |
| 18 | 0.22 | 20 | 10 | 80 | 20 | 0.09 | 8 | 0.09 |
| 19 | 0.11 | 20 | 10 | 80 | 20 | 0.08 | 8.5 | 0.10 |
| 20 | 0.11 | 20 | 10 | 80 | 20 | 0.09 | 7.5 | 0.09 |

A mechanistic model was developed which describes the reduction based on reaction kinetics. Besides the inherent effect of the protein concentration and the molar ratio of the reducing agent the model includes the effect of the conductivity and the temperature on the reaction rate constants. The model parameters were determined by fit to experimental data. Model simulations were then used to describe the combined effect of the protein concentration, the temperature, and the ionic strength at a significant number of conditions.

A correlation describing the minimum concentration required at a given temperature and ionic strength in order to obtain a satisfactory reduction was obtained. Satisfactory in this case means that the concentration of the start protein is reduced to <2% within approximately 6 h. The large number of data points created using simulation allowed for a detailed correlation, hence the specific (unusual) shape of the correlation.

Figure 5:
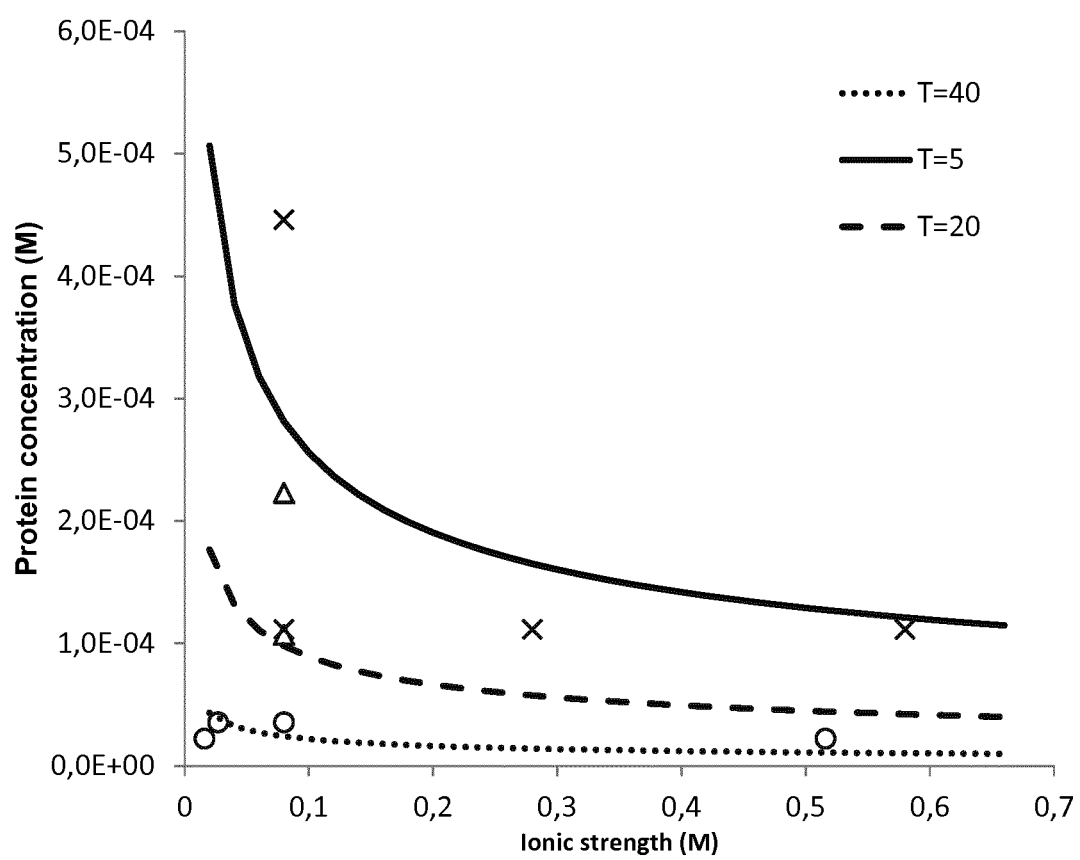
FIG. 5 shows the correlation for the minimum protein concentration during the reduction as function of ionic strength at three different temperatures. Experimental examples from table 1 are presented with the following symbols: X: T=5° C., Δ: T=20° C. and ○: T=40° C.

The following correlation was derived and is illustrated by FIG. 5.

$$C_{min} = a * I^{-a_1} \exp(-b*T), \text{ wherein}$$

T is the temperature in degrees Celsius
I is the ionic strength in M (mol/L)
$C_{min}$ is M (mol/L) and the constants are
$a = 0.137*10^{-3} M^{1.425}$
$a_1 = 0.425$
$b = 0.070\ C^{-1}$ The calculation of $C_{min}$ for exp. 9 and 16 from table 1 and FIG. 9 are exemplified here below.
$C_{min}$ is calculated according to the following correlation described above wherein $C_{min} = a*I^{-a_1}\exp(-b*T)$,
Calculation for exp. 9

$$I = 0.08(NaCl) + 0.02*1/(1+10^{(7.4-7.8)})(\text{trietanolamine}) = 0.09\ M$$

$$T = 5°\ C.:$$

$$C_{min} = 0.137*10^{-3}*0.09^{0.425}*\exp(-0.070*5) = 0.26*10^{-3}\ M = 0.26\ mM$$

$C_P$ for exp. 9 was 0.11 mM which is below $C_{min}$ and thus outside the range of favoured conditions according to the present invention.

Calculation for exp. 16

$I = 0.516(NaCl) + 0.004 * 1/(1+10^{(7.4-7.8)})(\text{trietanolamine}) = 0.52$ M $T = 40°$ C.:

$C_{min} = 0.137 * 10^{-3} * 0.52^{-0.425} * \exp(-0.070 * 40) = 0.01 * 10^{-3}$ M $= 0.01$ mM $C_P$ for exp. 16 is 0.02 which is above $C_{min}$ and within the range of favoured conditions according to the present inventions.

Figure 6:
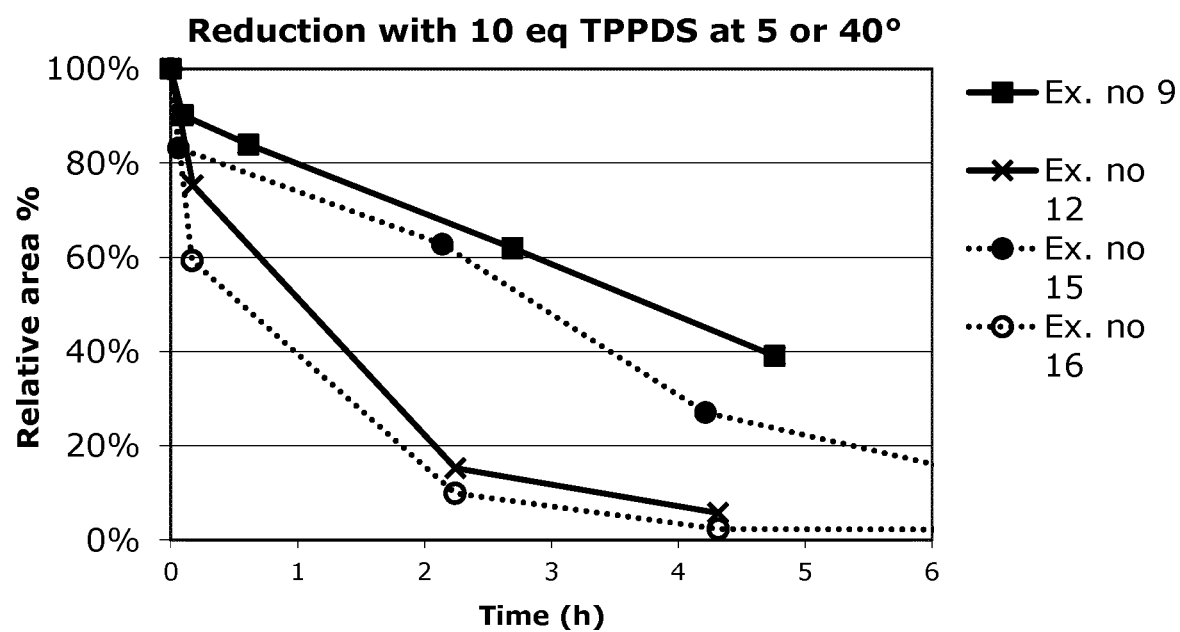
FIG. 6 shows the reduction of GH-L101C-S-Glutathion under the conditions of experiments 9, 12, 15 and 16 from table 1. The reaction was monitored by AIE-HPLC, and the relative area % of the starting material is plotted versus reaction time. Solid line is 5° C. and dotted line is 40° C.

The usability is further illustrated by FIG. 6, which shows two experiments with a protein concentration ($C_P$) higher than $C_{min}$ (Exp. 12 and 16) and two experiments with a $C_P$ lower than $C_{min}$ (Exp. 9 and 15). In the experiments 12 and 16 the starting material (protein-S-S-Cap) is converted to below 2% within a reaction time of 6 h. Experiments 12 and 16 demonstrates that a useful reaction yield can be obtained with either a high protein concentration (exp. 12) to compensate for a low temperature or by having both a high ionic strength and a higher temperature to compensate for a low protein concentration (exp. 16).

Example 6

Defining Minimum Protein Concentration for the Conjugation Reaction

As seen in the earlier examples (such as Example 3) a satisfactory conjugation reaction was obtained by using a higher protein concentration also in the conjugation reaction allowing use of fewer equivalents of the activated chemical moiety (Z*) exemplified by and albumin binding side chain. Again an influence of the ionic strength and the temperature was investigated and a satisfactory conjugation reaction in this case means that the concentration of the start protein (Protein-SH) is reduced to <5% within approximately 10 h. As standard, Triethanolamine (20 mM), NaCl (80 mM) and KI (0.5 M) was included providing a ionic strength around 0.5.

TABLE 2

Examples of different conditions tested for the conjugation reaction. The conditions for the conjugation reactions include protein concentration (Cp), Temperature (Temp), the number of equivalents (n) of the side chain Z*, and ionic strength in the conjugation mix (including buffers but excluding protein and sides chain) for conjugation experiments 1-21. The examples 10-21 are plotted in FIG. 7. The calculated $C_{min}$ as described below is also included for comparison.

| Exp. | $C_P$ (mM) | Temp (° C.) | n (Z*) | NaCl/ Guanidinium HCl (mM) | KI (mM) | Trietanolamine (mM) | Ionic strength (M) | pH | $C_{min}$ (mM) |
|---|---|---|---|---|---|---|---|---|---|
| 1 | 0.11 | 30 | 3 | 80 | 450 | 20 | 0.55 | 7.0 | 0.03 |
| 2 | 0.11 | 30 | 3 | 80 | 450 | 20 | 0.54 | 8.0 | 0.03 |
| 3 | 0.45 | 20 | 2.2 | 80 | 460 | 20 | 0.55 | 7.4 | 0.04 |
| 4 | 0.45 | 20 | 2.2 | 280 | 460 | 20 | 0.75 | 7.4 | 0.03 |
| 5 | 0.45 | 20 | 2 | 80 | 200 | 20 | 0.29 | 7.4 | 0.05 |
| 6 | 0.45 | 20 | 2 | 580 | 200 | 20 | 0.79 | 7.4 | 0.03 |
| 7 | 0.45 | 20 | 2 | 580* | 200 | 20 | 0.79 | 7.4 | 0.03 |
| 8 | 0.45 | 20 | 2 | 400 | 200 | 20 | 0.61 | 7.4 | 0.03 |
| 9 | 0.22 | 20 | 2 | 80 | 320 | 20 | 0.41 | 7.4 | 0.04 |
| 10 | 0.08 | 20 | 3.6 | 80 | 450 | 20 | 0.55 | 7.0 | 0.04 |
| 11 | 0.08 | 20 | 3.6 | 80 | 450 | 20 | 0.54 | 8.0 | 0.04 |
| 12 | 0.22 | 20 | 4.7 | 80 | 160 | 20 | 0.25 | 7.4 | 0.05 |
| 13 | 0.22 | 20 | 4.7 | 280 | 160 | 20 | 0.45 | 7.4 | 0.04 |
| 14 | 0.11 | 5 | 4 | 80 | 220 | 20 | 0.31 | 7.4 | 0.07 |
| 15 | 0.45 | 5 | 4 | 80 | 750 | 20 | 0.84 | 7.4 | 0.05 |
| 16 | 0.11 | 5 | 4 | 280 | 220 | 20 | 0.51 | 7.4 | 0.06 |
| 17 | 0.11 | 5 | 4 | 580 | 220 | 20 | 0.81 | 7.4 | 0.05 |
| 18 | 0.04 | 40 | 4 | 27 | 70 | 7 | 0.10 | 7.4 | 0.07 |
| 19 | 0.04 | 40 | 4 | 427 | 70 | 7 | 0.50 | 7.4 | 0.02 |
| 20 | 0.11 | 40 | 4 | 20 | 220 | 5 | 0.24 | 7.4 | 0.03 |
| 21 | 0.05 | 40 | 4 | 320 | 110 | 5 | 0.43 | 7.4 | 0.02 |

*This example is the only one with guanidinium HCl

Figure 7:
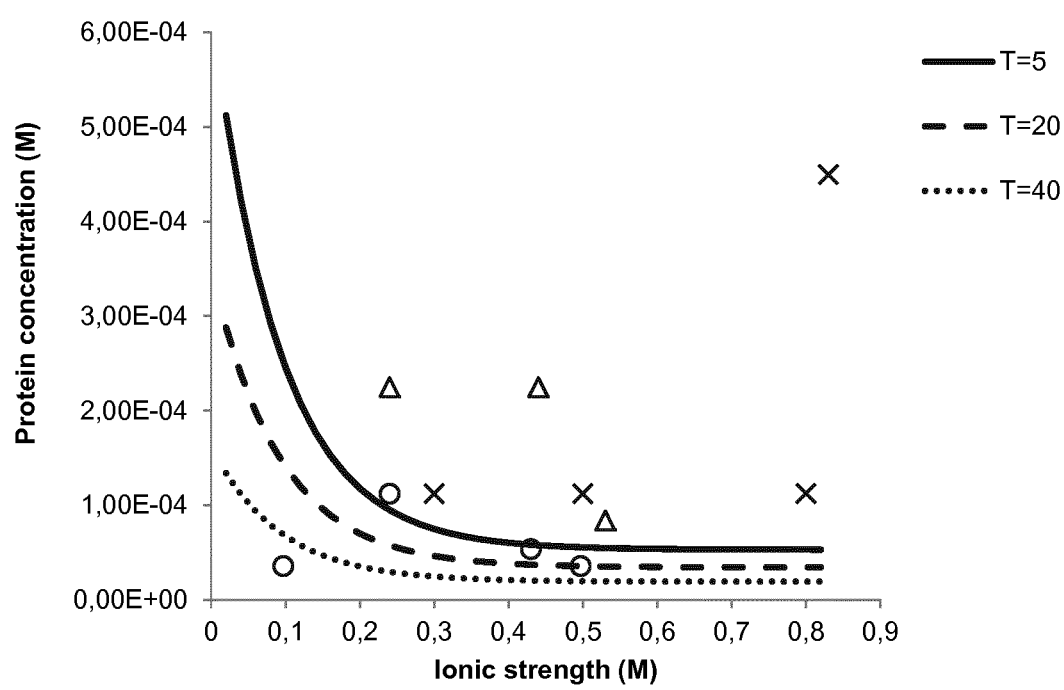
FIG. 7 shows the correlation for the minimum protein concentration during the conjugation as function of ionic strength at three different temperatures. Experimental examples from table 2 are presented with the following symbols; X: T=5° C., Δ: T=20° C. and ○: T=40° C.

The conditions for the conjugation reaction include protein concentration (Cp), Temperature (Temp) in Celsius, the number of equivalents (n) of the side chain and ionic strength e.g. the concentration of salts in the reduction mix (including buffers but excluding protein and side chain components. Based on the conjugation conditions tested in experiment 1-20 of table 2 a mechanistic model was developed using the same approach as for the reduction. Simulation was used to generating substantial amount of data using enabling development of a correlation describing the minimum protein concentration required at given combinations of temperature and ionic strength in order to obtain a satisfactory conjugation. Satisfactory in this case means that the concentration of the reduced protein is reduced to <5% within approximately 10 h. Based on the data obtained suitable conditions for the conjugation reaction can be defined using the following definition for the minimum protein concentration ($C_{min}$) depending on the temperature and Ionic strength as illustrated by FIG. 7.

$$C_{min} = 6.96 * 10 \text{-} 4 * \exp(-0.0396 * 5 - 10.9 * I) + 6.12 * 10 \text{-} 5 * \exp(-0.0289 * 5)$$

$$= 6.96 * 10 \text{-} 4 * \exp(-1.98 - 10.9 * I) + 5.30 * 10 \text{-} 5$$

$$C_{min} = a * \exp(-b_1 * T - b_2 * I) + d * \exp(-d_1 * T)$$

wherein T is the temperature in degrees Celsius, I is the ionic strength in M (mol/L) and $C_{min}$ is the minimal protein concentration in M (mol/L)

a=6.96*10$^{-4}$ M
b$_1$=0.0396° C.$^{-1}$
b$_2$=10.9 M$^{-1}$
d=6.12*10$^{-5}$ M
d$_1$=0.0289° C.$^{-1}$

The calculations for conjugation experiments 15 and 18 are shown here below:

Calculation for exp. 15

$$I=0.08(\text{NaCl})+0.75(\text{KI})+0.02*1/(1+10^{(7.4-7.8)})(\text{trietanolamine})=0.84 \text{ M}$$

$$T=5° \text{ C.:}$$

$$C_{min}=6.96*10-4*\exp(-0.0396*5-10.9*0.84)+6.12*10-5*\exp(-0.0289*5)=0.05*10-3 \text{ M}=0.05 \text{ mM}$$

The protein concentration ($C_P$) in exp 15 was 0.45 M, clearly above $C_{min}$ as calculated.

Calculation for exp. 18

$$I=0.027(\text{NaCl})+0.07(\text{KI})+0.007*1/(1+10^{(7.4-7.8)})(\text{trietanolamine})=0.10 \text{ M}$$

$$T=40° \text{ C.:}$$

$$C_{min} = 6.96*10\text{-}4*\exp(-0.0396*40-10.9*0.10) + 6.12*10\text{-}5*\exp(-0.0289*40)$$

$$= 0.70*10\text{-}3 \text{ M}$$

$$= 0.07 \text{ mM}$$

The protein concentration ($C_P$) in exp. 18 was 0.04 mM which is below $C_{min}$ of 0.10 M.

Figure 8:
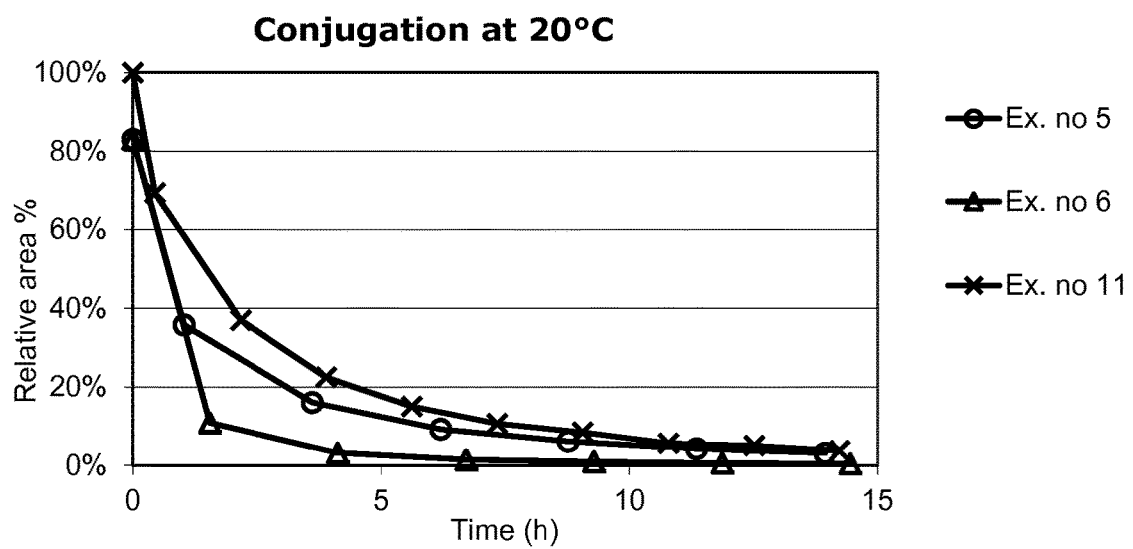
FIG. 8 shows examples of the conjugation reaction where the relative content of the reduced protein (GH-L101C-SH) is monitored.
Figure 8:
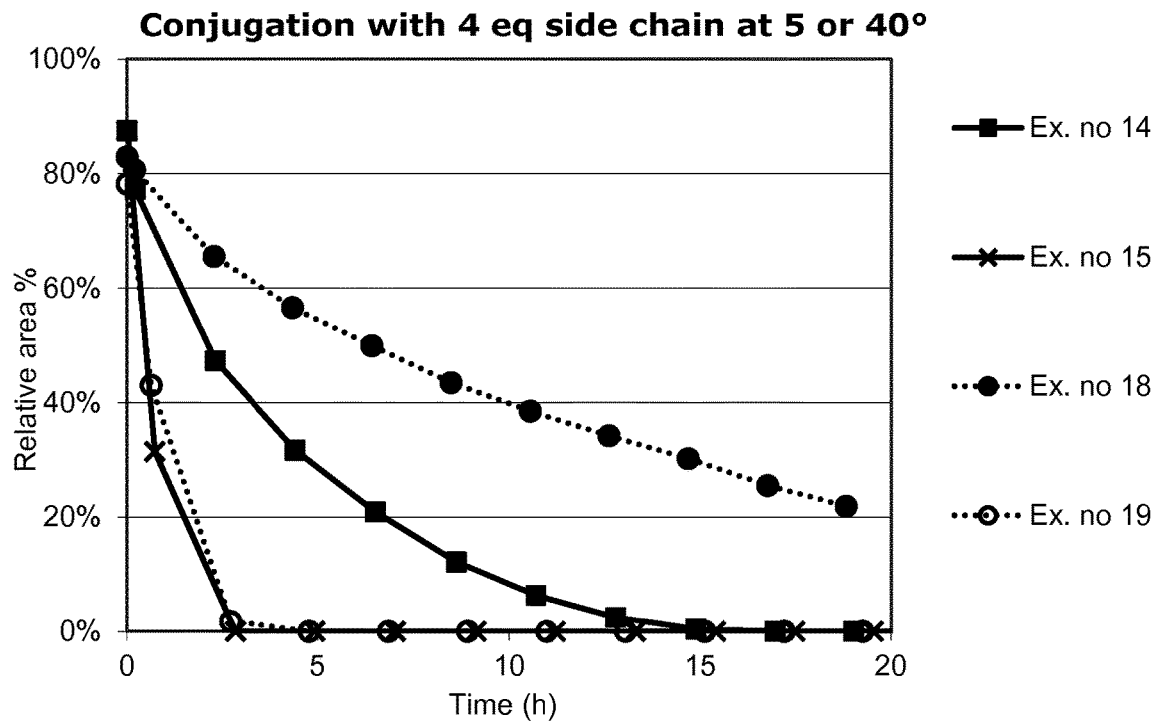

The usability of the correlation is illustrated by FIGS. 8A and 8B showing a series of experiments testing different conjugation conditions. In experiment 11 the amount of reduced protein is reduced to around 5% of starting material after approximately 10 h at 20° C. ($C_P$=0.08 mM and 3.6 eq of side chain). In experiment 5, the reaction is faster which is obtained by using an increased amount of reduced protein ($C_P$) even if the number of equivalents of the side chain is reduced to 2 eq. As seen by experiment 6, compared to experiment 5, an increase in ionic strength further accelerates the reaction. In experiment 14, 15 and 19 (FIG. 8B) the protein concentration ($C_P$) is higher than $C_{min}$ while experiment 18 demonstrates the low efficacy of an experiment with $C_P$ below $C_{min}$. In the latter the reaction was very slow and after 20 h approximately 20% starting material still remains. In experiment 19 the ionic strength is increased but the $C_P$ and T kept constant compared to exp. 18 resulting in a higher reaction rate and thus a conversion of starting material to below 5% in less than 3 h. The two examples at 5° C. both have a $C_P$ above $C_{min}$, and the conversion of starting material to below 5% is obtained in approximately 10 h or less. However, the increase in $C_P$ and ionic strength in exp. 15 compared to exp. 14 resulted in an even more efficient conversion of starting material.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for preparing a protein conjugate wherein a protein (P) is covalently bound to a chemical moiety (Z) via a thioether, comprising the steps of:
   a) obtaining a composition of a mixed di-sulfide comprising the protein,
   b) adding a reducing agent to the composition to obtain a reduction mix, wherein the reducing agent is a phosphine,
   c) allowing a reduction reaction to occur,
   d) obtaining a solution comprising a reduced protein (P-SH),
   e) optionally removing molecules with a molecular weight below 10 kDa from the solution,
   f) adding an activated chemical moiety (Z*) to the solution comprising the reduced protein and obtaining a conjugation mix including 1-4 equivalents of the activated chemical moiety (Z*) relative to the reduced protein,
   g) allowing a conjugation reaction to occur to generate a conjugated protein (P-S-Z), and
   h) obtaining a preparation of the conjugated protein (P-S-Z),
   wherein the reduction mix of step b) has a concentration of the mixed di-sulfide of at least Cmin,
   wherein Cmin is defined by: $Cmin = a \cdot I^{-a_1} \exp(-b \cdot T)$, wherein T is the temperature in degrees Celsius, I is ionic strength (M) of the reduction mix, $a = 0.137 \cdot 10^{-3}$ $M^{1.425}$, $a_1 = 0.425$ and $b = 0.070°\, C.^{-1}$,
   wherein at least one step is performed in a cross flow filtration system, and
   wherein the activated chemical moiety (Z*) is an activated albumin binder.

2. The method according to claim 1, wherein the mixed di-sulfide is a protein with a capped free cysteine (P-S-S-Cap).

3. The method according to claim 2, wherein the Cap is derived from cysteine, cysteamine or glutathione.

4. The method according to claim 1, wherein the conjugation mix of f) has a concentration of the reduced protein of at least Cmin, where Cmin is defined by:

$$Cmin = a \cdot \exp(-b1 \cdot T - b2 \cdot I) + d \cdot \exp(-d1 \cdot T)$$

wherein T is the temperature in degrees Celsius, I is the ionic strength (M) of the conjugation mix, $a = 6.96 \cdot 10{-4}$ M, $b1 = 0.0396°\, C.^{-1}$, $b2 = 10.9\, M^{-1}$, $d = 6.12 \cdot 10^{-5}$ M and $d1 = 0.0289°\, C.^{-1}$.

5. The method according to claim 1, wherein the reducing agent is a triarylphosphine.

6. The method according to claim 1, wherein the amount of the reducing agent included in the reduction mix of step b) is at most 10 equivalents of the protein (P-S-S-Cap).

7. The method according to claim 1, wherein the activated chemical moiety (Z*) is a halogenated albumin binder including Br, I or Cl.

8. The method according to claim 1, wherein the conjugation mix of step f) includes at most 3 equivalent of the activated chemical moiety (Z*), relative to the mixed di-sulfide.

9. The method according to claim 1, where step e) is diafiltration performed using a cellulose membrane.

10. The method according to claim 9, wherein the diafiltration performed in step (e) use a diafiltration buffer which does not include a reducing agent.

11. The method according to claim 1, wherein the composition of step a), the reduction mix of step b), the solution of step d), the conjugation mix of step f) and/or the preparation of step h) comprise triethanolamine.

12. The method according to claim 1, wherein the composition of step a), the reduction mix of step b), the solution of step d), the conjugation mix of step f) and/or the preparation of step h) have pH 7.0-8.0.

13. The method according to claim 1, wherein the protein is a growth hormone polypeptide comprising a L101C point mutation.

14. The method according to claim 5, wherein the reducing agent is disodium triphenylphosphine-3,3'-disulfonate (TPPDS).

15. The method according to claim 1, wherein the activated chemical moiety (Z*) is a halogenated albumin binder including Iodine (I).

16. The method according to claim 1, wherein the activated chemical moiety (Z*) is an iodoacetamide of an albumin binder.

17. The method according to claim 1, wherein the activated chemical moiety (Z*) is selected from the group consisting of:

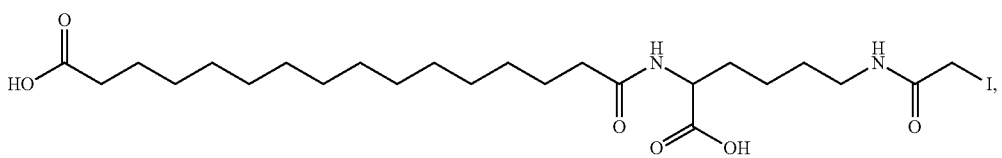

-continued
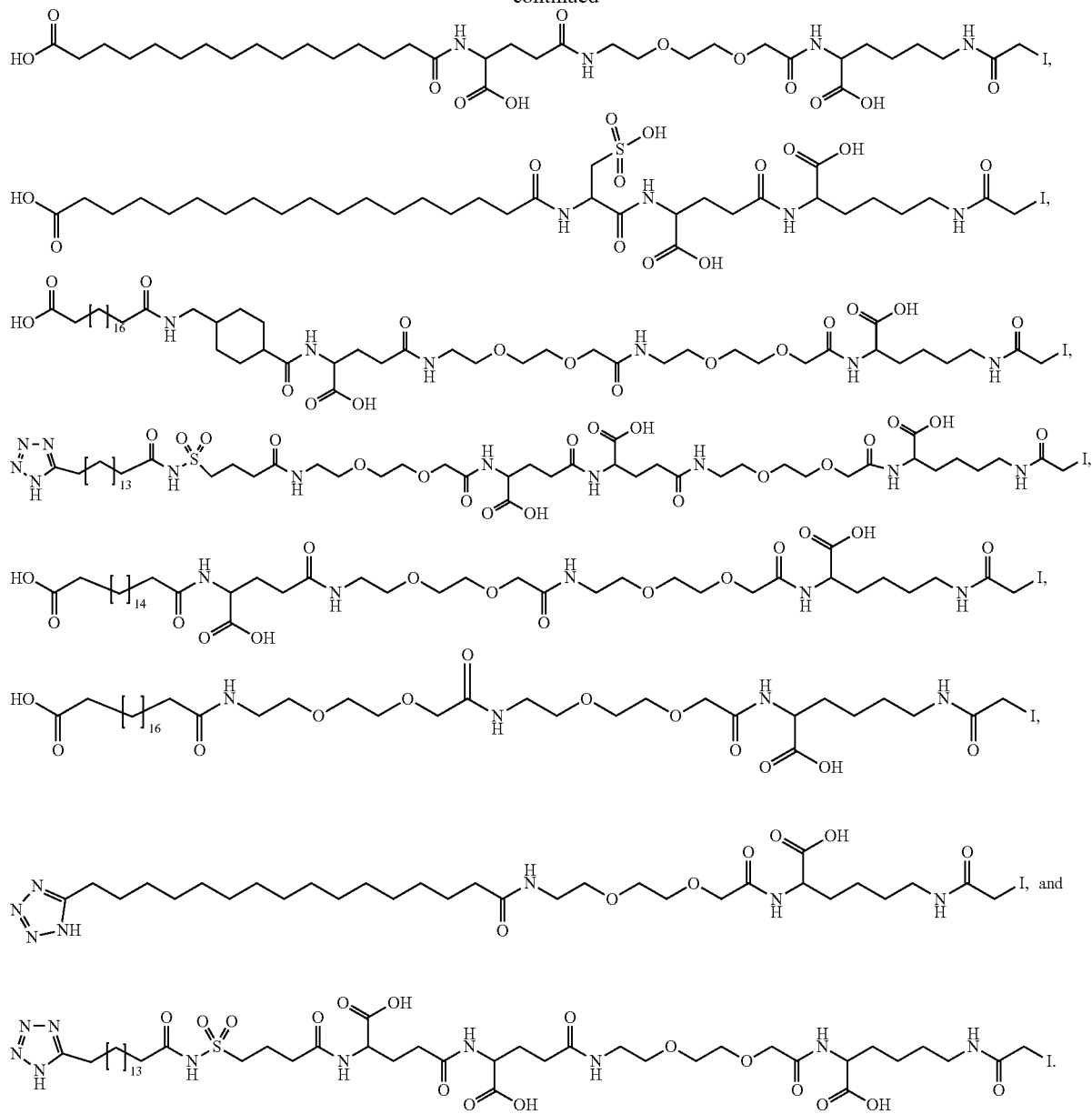
18. The method according to claim 1, wherein the activated chemical moiety (Z*) is selected from the group consisting of:
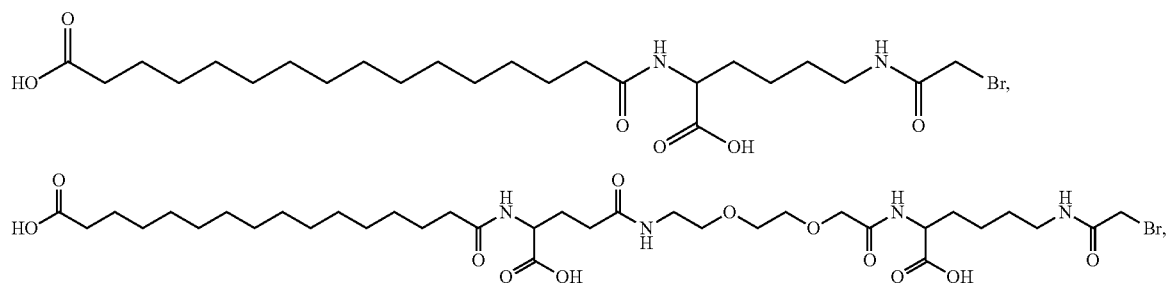

-continued
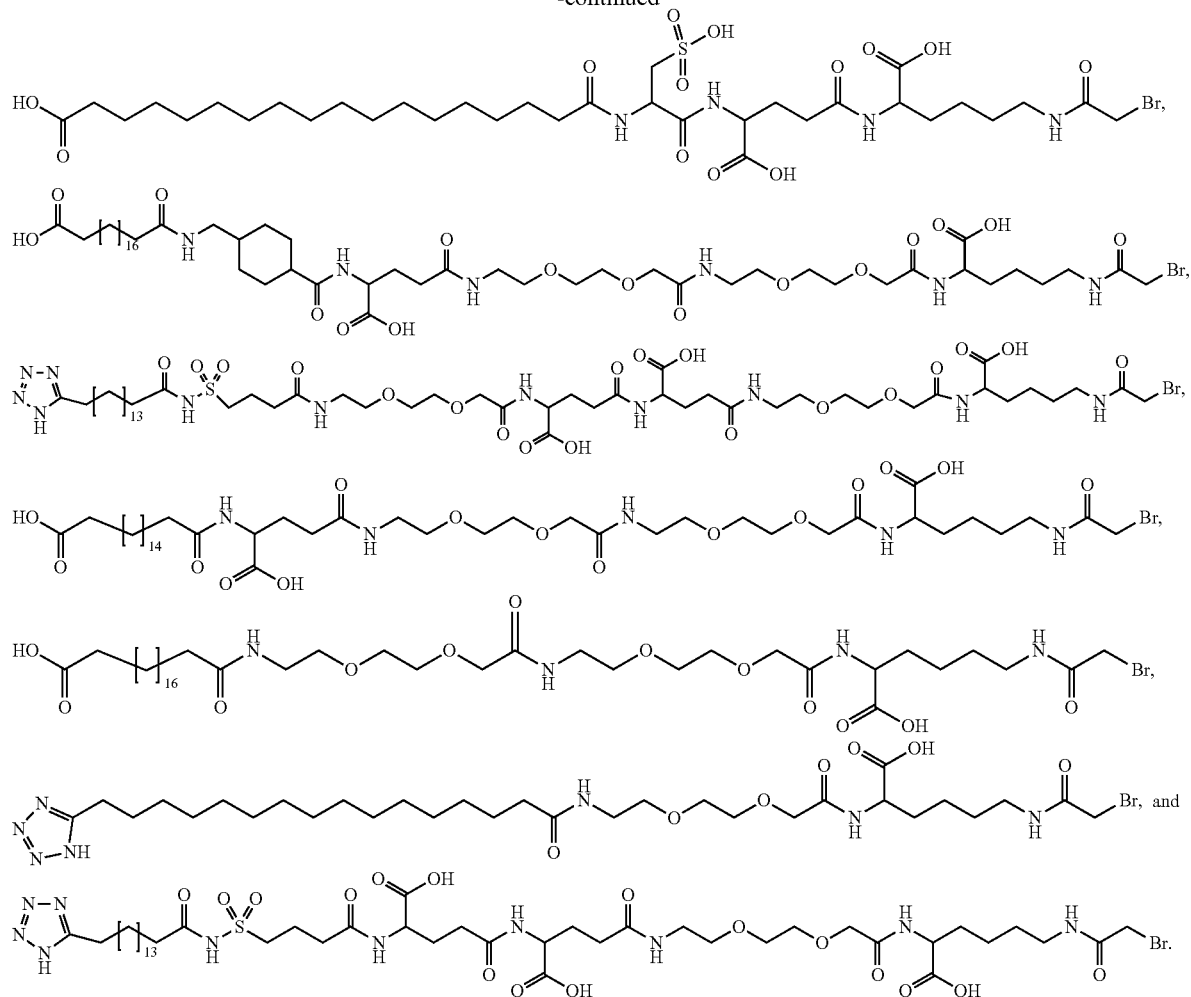
19. The method of claim 1, wherein the conductivity of the solution of d) is 10 mS/cm at 22° C.
20. The method of claim 1, wherein the mixed di-sulfide composition comprises a buffer selected from the group consisting of BES, HEPES, IVIES, Phosphate, Citrate, Bis-Tris and triethanolamine.
* * * * *

UNITED STATES PATENT AND TRADEMARK OFFICE
CERTIFICATE OF CORRECTION

PATENT NO. : 11,219,690 B2
APPLICATION NO. : 15/103482
DATED : January 11, 2022
INVENTOR(S) : Charlotte Schou Hunneche et al.

Page 1 of 1

It is certified that error appears in the above-identified patent and that said Letters Patent is hereby corrected as shown below:

In the Claims

At Column 39, Claim number 20, Line number 46, please replace with the following:
"consisting of BES, HEPES, MES, Phosphate, Citrate,"

Signed and Sealed this
Thirtieth Day of August, 2022

Katherine Kelly Vidal
*Director of the United States Patent and Trademark Office*